United States Patent
Tang et al.

(10) Patent No.: US 12,263,027 B2
(45) Date of Patent: Apr. 1, 2025

(54) SCANNING APPARATUS, METHOD, AND SYSTEM

(71) Applicant: SHANGHAI UNITED IMAGING HEALTHCARE CO., LTD., Shanghai (CN)

(72) Inventors: Yang Tang, Shanghai (CN); Kai Cui, Shanghai (CN); Jing Yan, Shanghai (CN); Guanji Leng, Shanghai (CN); Lu Chen, Shanghai (CN); Juan Feng, Shanghai (CN); Haihua Zhou, Shanghai (CN); Zhou Yuan, Shanghai (CN); Le Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 245 days.

(21) Appl. No.: 18/054,123

(22) Filed: Nov. 9, 2022

(65) Prior Publication Data
US 2023/0092496 A1    Mar. 23, 2023

Related U.S. Application Data

(63) Continuation of application No. PCT/CN2021/092898, filed on May 10, 2021.

(30) Foreign Application Priority Data

May 9, 2020  (CN) .......................... 202010385474.8
May 9, 2020  (CN) .......................... 202010387550.9
May 9, 2020  (CN) .......................... 202010387567.4

(51) Int. Cl.
A61B 6/00    (2024.01)
A61B 6/02    (2006.01)
(Continued)

(52) U.S. Cl.
CPC ................ *A61B 6/54* (2013.01); *A61B 6/027* (2013.01); *A61B 6/035* (2013.01); *A61B 6/4085* (2013.01);
(Continued)

(58) Field of Classification Search
CPC ......... A61B 6/54; A61B 6/035; A61B 6/4085; A61B 6/4441; A61B 6/4447;
(Continued)

(56) References Cited

U.S. PATENT DOCUMENTS 5,430,783 A   7/1995   Hu et al.
7,711,083 B2  5/2010   Heigl et al.
(Continued)

FOREIGN PATENT DOCUMENTS

CN    202288320 U    7/2012
CN    106430000 A    2/2017
(Continued)

OTHER PUBLICATIONS

The Extended European Search Report in European Application No. 21802999.9 mailed on Oct. 24, 2023, 9 pages.
(Continued)

*Primary Examiner* — Dani Fox
*Assistant Examiner* — Mamadou Faye
(74) *Attorney, Agent, or Firm* — METIS IP LLC

(57) ABSTRACT

A scanning apparatus (110), a medical image obtaining method, and a medical image obtaining system (100) are provided. The scanning apparatus (110) comprises a gantry, a controller, a C-shaped arm, a radiation source (112), and a detector (113). The radiation source (112) and the detector (113) are arranged at both ends of the C-shaped arm. The C-shaped arm is connected to the gantry. The controller is
(Continued)

configured to control a motion of the gantry to drive the C-shaped arm to move so as to scan a target object.

20 Claims, 16 Drawing Sheets

(51) Int. Cl.
*A61B 6/03* (2006.01)
*A61B 6/40* (2024.01)

(52) U.S. Cl.
CPC .......... *A61B 6/4441* (2013.01); *A61B 6/4447* (2013.01); *A61B 6/4458* (2013.01); *A61B 6/4476* (2013.01); *A61B 6/5205* (2013.01); *A61B 6/4464* (2013.01)

(58) Field of Classification Search
CPC ... A61B 6/4476; A61B 6/5205; A61B 6/4464; A61B 6/032; A61B 6/4458
See application file for complete search history.

(56) References Cited

U.S. PATENT DOCUMENTS

| | | | |
|---|---|---|---|
| 10,307,121 B2* | 6/2019 | Brudniok | A61B 6/4458 |
| 2004/0047449 A1 | 3/2004 | Hagiwara | |
| 2004/0208277 A1 | 10/2004 | Morikawa et al. | |
| 2009/0185662 A1 | 7/2009 | Gross et al. | |
| 2010/0232565 A1 | 9/2010 | Ye et al. | |
| 2010/0322498 A1 | 12/2010 | Wieczorek et al. | |
| 2011/0182400 A1 | 7/2011 | Forthmann et al. | |
| 2011/0286573 A1 | 11/2011 | Schretter et al. | |
| 2012/0121062 A1* | 5/2012 | Sowards-Emmerd | G06T 11/006 378/4 |
| 2014/0153690 A1* | 6/2014 | Claus | A61B 6/027 378/19 |
| 2015/0139396 A1 | 5/2015 | Klingenbeck | |
| 2017/0053414 A1* | 2/2017 | Flohr | A61B 6/12 |
| 2019/0029629 A1 | 1/2019 | Johnson et al. | |
| 2020/0054297 A1* | 2/2020 | Martinez Ferreira | A61B 6/4441 |
| 2020/0187885 A1 | 6/2020 | Tang et al. | |

FOREIGN PATENT DOCUMENTS

| | | |
|---|---|---|
| CN | 107714062 A | 2/2018 |
| CN | 209652877 U | 11/2019 |
| CN | 110811655 A | 2/2020 |
| CN | 110833426 A | 2/2020 |
| CN | 111528881 A | 8/2020 |
| CN | 111528882 A | 8/2020 |
| CN | 111528890 A | 8/2020 |
| DE | 102011086754 A1 | 5/2013 |
| JP | 2002058666 A | 2/2002 |
| JP | 2008125909 A | 6/2008 |
| WO | 2020070211 A1 | 4/2020 |
| WO | 2021136162 A1 | 7/2021 |

OTHER PUBLICATIONS

International Search Report in PCT/CN2021/092898 mailed on Aug. 11, 2021, 8 pages.
Written Opinion in PCT/CN2021/092898 mailed on Aug. 11, 2021, 12 pages.
J. Gregor et al., Conebeam X-ray Computed Tomography with an Offset Detector Array, IEEE International Conference on Image Processing, II_803- II_806, 2003.

* cited by examiner

SCANNING APPARATUS, METHOD, AND SYSTEM

CROSS-REFERENCE TO RELATED APPLICATION

This application is a continuation of International Patent Application No. PCT/CN2021/092898, filed on May 10, 2021, which claims priority of Chinese Patent Applications No. 202010387567.4, No. 202010385474.8, and No. 202010387550.9, both filed on May 9, 2020, the contents of each of which are entirely incorporated herein by reference.

TECHNICAL FIELD

The present disclosure relates to the field of medical imaging, and in particular, to a scanning apparatus, method, and system.

BACKGROUND

With the development of modern medicine, diagnosis and treatment work of a medical institution increasingly depends on an examination of medical images. A medical imaging device in a medical imaging system usually includes a plurality of systems (e.g., a data acquirement system, an image reconstruction system, an image display system, and a storage system, etc.). A reconstruction field of view in the image reconstruction system is limited by a size of a detector of the medical scanning apparatus.

A C-shaped arm is a bracket with a C shape, which can be used to carry a device. For example, a radiation source and a ray detector are respectively installed on the C-shaped arm to achieve a purpose of medical examination or treatment. There is only one beam scanning area between the radiation source and the ray detector. In order to expand the scanning area, it is necessary to use the C-shaped arm to drive the radiation source and the detector to rotate.

An X-ray device is a device that can be used to examine and diagnose various parts of an object. A device that uses X-rays as the basis for the examination and diagnosis, and controls the X-rays to perform a radiological examination and a radiotherapy on a human tissue can help doctors to determine a patient's specific condition. The X-ray device may include a mammography X-ray device, a dental (oral) X-ray device, a digital subtraction angiography (DSA) X-ray device, etc. An operator usually adjusts a detector and a radiation source through a lift assembly of the C-shaped arm to meet imaging requirements of different scenes. An overall size of the lift assembly has a great influence on the operation of the C-shaped arm (or the C-shaped main body part).

SUMMARY

One of the embodiments of the present disclosure provides a scanning apparatus, including a gantry, a controller, a C-shaped arm, a radiation source, and a detector. The radiation source and the detector are arranged at both ends of the C-shaped arm. The C-shaped arm is connected to the gantry. The controller is configured to control a motion of the gantry to drive the C-shaped arm to move so as to scan a target object.

In some embodiments, the scanning apparatus is a cone-beam computed tomography scanning apparatus, and the gantry has a deflection mode and a rotation mode. In the deflection mode, the gantry drives the radiation source and the detector to deflect around a center point of the detector. In the rotation mode, the gantry drives the radiation source and the detector to rotate around a center of interest of the target object to scan the target object and obtain scanning data of the target object. The the radiation source and the detector have a first reconstruction field of view (FOV) before the deflection, the radiation source and the detector have a second reconstruction FOV after the deflection, and the second reconstruction FOV is larger than the first reconstruction FOV.

In some embodiments, a scanning view of a single gantry after the deflection of the radiation source and the detector covers at least half of the second reconstruction FOV.

In some embodiments, the cone-beam computed tomography scanning apparatus is a digital subtraction angiography scanner or a mobile C-shaped arm machine.

In some embodiments, a deflection angle of the deflection is adjustable.

In some embodiments, under the control of the controller, the radiation source at one end of the C-shaped arm is configured to move in a first direction while performing a circular scanning motion.

In some embodiments, under the control of the controller, the radiation source is configured to scan along a spiral trajectory.

In some embodiments, under the control of the controller, the radiation source alternately performs a circular motion in a clockwise direction and a counterclockwise direction while moving in the first direction, so that the radiation source scans along a reciprocating spiral trajectory.

In some embodiments, the first direction is perpendicular to a circumferential plane formed when the radiation source has a circular motion.

In some embodiments, the first direction forms a first included angle with a perpendicular line of a circumferential plane formed when the radiation source has a circular motion, and the first included angle is smaller than a preset threshold.

In some embodiments, the first direction is an extension direction of a scanning bed.

In some embodiments, the controller is configured to control the radiation source to move in the first direction while performing the circular scanning motion within a scanning range, and the scanning range covers a target scanning range.

In some embodiments, at least one of the detector or the radiation source is connected to the C-shaped arm through a lift assembly. The lift assembly includes a shell, a driving assembly accommodated in the shell, and an arm adjustment assembly. The arm adjustment assembly moves under a driving of the driving assembly. The arm adjustment assembly includes an intermediate arm section, a target arm section, and a linkage assembly disposed between the intermediate arm section and the target arm section. The intermediate arm section moves in a first direction under the driving of the driving assembly. When the intermediate arm section moves in the first direction, the target arm section is driven to move in the first direction by the linkage assembly. Projections of the intermediate arm section and the target arm section respectively in the first direction at least partially overlap, and. The target arm section is connected to the detector or the radiation source.

In some embodiments, the linkage assembly includes a first support component and a second support component arranged on the intermediate arm section, a first flexible traction component connected to the first support component, and a second flexible traction component connected to the second support component. One end of the first flexible traction component is connected to the shell, and the other end of the first flexible traction component is connected to the target arm section. One end of the second flexible traction component is connected to the shell, and the other end of the second flexible traction component is connected to the target arm section.

In some embodiments, the first support component or the second support component includes a pulley or a sprocket. The first flexible traction component or the second flexible traction component includes a rope connected to the pulley or a chain connected to the sprocket.

In some embodiments, the linkage assembly further includes a first sliding block, and a first guiding rail matched with the first sliding block. The first sliding block is arranged on one of the intermediate arm section and the target arm section, and the first guiding rail is arranged on the other one of the intermediate arm section and the target arm section.

In some embodiments, the lift assembly further includes a transmission assembly disposed between the driving assembly and the intermediate arm section configured for a transmission between the driving assembly and the intermediate arm section.

In some embodiments, the transmission assembly includes a screw nut structure.

In some embodiments, the screw nut structure includes a nut rotatable relative to the shell, and a screw located at a fixed location relative to the intermediate arm section. The nut is threadedly connected to the screw, and the nut is driven by the driving assembly.

In some embodiments, the lift assembly further includes a second sliding block disposed between the shell and the intermediate arm section and a second guiding rail matched with the second sliding block, wherein the second sliding block is arranged on one of the shell and the intermediate arm section, and the second guiding rail is arranged on the other one of the shell and the intermediate arm section.

One of the embodiments of the present disclosure provides a medical image obtaining method. The method is implemented by a cone-beam computed tomography scanning apparatus. The cone-beam computed tomography scanning apparatus includes a radiation source and a detector. The method includes: deflecting the radiation source and the detector around a center point of the detector; and rotating the deflected radiation source and the deflected detector around a center of interest of a target object to scan the target object and obtain scanning data of the target object. The radiation source and the detector have a first reconstruction FOV before the deflection, the radiation source and the detector have a second reconstruction FOV after the deflection, and the second reconstruction FOV is larger than the first reconstruction FOV.

In some embodiments, a scanning view of a single gantry after the deflection of the radiation source and the detector covers at least half of the second reconstruction FOV.

In some embodiments, the second reconstruction FOV includes a repeatedly scanned area. The method further includes reconstructing the scanning data of the target object to obtain a reconstruction image of the target object. The reconstruction image includes an image region corresponding to the repeatedly scanned area, and the image region is reconstructed by further includes: weighting the scanning data of the repeatedly scanned area based on a preset weight curve.

In some embodiments, the preset weight curve is related to positions at the detector corresponding to the repeatedly scanned area. The preset weight curve is determined by: determining, starting from the radiation source, two tangent lines tangent to the repeatedly scanned area, the two tangent lines passing through a first point and a second point of the detector, respectively; determining, starting from the radiation source, a straight line passing through the center of interest and a third point of the detector, the first point being located at an edge of the detector, the second point being located in a non-edge area of the detector, and the third point being located between the first point and the second point; setting a weight of the scanning data corresponding to the first point as a; setting a weight of the scanning data corresponding to the second point as b; setting a weight of the scanning data corresponding to the third point as c; $0 \leq a < c < b \leq 1$, and determining a weight curve from the first point to the second point of the detector as the preset weight curve according to the set weights.

In some embodiments, the detector is a flat panel detector.

In some embodiments, the cone-beam computed tomography scanning apparatus is a digital subtraction angiography scanner or a mobile C-shaped arm machine.

One of the embodiments of the present disclosure provides a system for obtaining a medical image. The system is configured to control a cone-beam computed tomography scanning apparatus. The cone-beam computed tomography scanning apparatus including a radiation source and a detector. The system includes a deflection module configured to deflect the radiation source and the detector around a center point of the detector, and a rotation module configured to rotate the deflected radiation source and the deflected detector around a center of interest of the target object to scan the target object and obtain scanning data of the target object. The radiation source and the detector have a first reconstruction FOV before the deflection, the radiation source and the detector have a second reconstruction FOV after the deflection, and the second reconstruction FOV is larger than the first reconstruction FOV.

One of the embodiments of the present disclosure provides a device for obtaining a medical image. The device includes at least one processor and at least one storage device, the storage device is configured to store an instruction, and when the at least one processor executes the instruction, the processor implements the method for obtaining the medical image described in the present disclosure.

One of the embodiments of the present disclosure provides a cone-beam computed tomography scanner, including a robotic arm, a radiation source, and a detector. The robotic arm has a deflection mode and a rotation mode. In the deflection mode, the mechanical arm drives the radiation source and the detector to deflect around a center point of the detector. In the rotation mode, the robotic arm drives the deflected radiation source and the deflected detector to rotate around a center of interest of the target object to scan the target object and obtain scanning data of the target object. The radiation source and the detector have a first reconstruction FOV before the deflection, the radiation source and the detector have a second reconstruction FOV after the deflection, and the second reconstruction FOV is larger than the first reconstruction FOV.

In some embodiments, the cone-beam computed tomography scanner is a digital subtraction angiography scanner or a mobile C-shaped arm machine.

In some embodiments, the robotic arm is a KUKA robot.

In some embodiments, the robotic arm is a multi-degree-of-freedom robot.

One of the embodiments of the present disclosure provides a cone-beam computed tomography scanning apparatus, including: a radiation source and a detector; a deflection mechanism configured to deflect the radiation source and the detector around a center point of the detector; and a rotation mechanism configured to drive the deflected radiation source and the deflected detector to rotate around a center of interest of the target object to scan the target object and obtain scanning data of the target object. The radiation source and the detector have a first reconstruction FOV before the deflection, the radiation source and the detector have a second reconstruction FOV after the deflection, and the second reconstruction FOV being larger than the first reconstruction FOV.

One of the embodiments of the present disclosure provides a scanning system based on a C-shaped arm, including a gantry, a controller, a C-shaped arm, a radiation source and a ray detector. The radiation source and the ray detector arranged at both ends of the C-shaped arm. The C-shaped arm is connected to the gantry. the controller is configured to control a motion of the gantry to drive the C-shaped arm to move. Under the control of the controller, the radiation source at one end of the C-shaped arm can move in a first direction while performing a circular scanning motion.

In some embodiments, under the control of the controller, the radiation source can scan along a spiral trajectory.

In some embodiments, under the control of the controller, the radiation source can scan along a reciprocating spiral trajectory, that is, the radiation source alternately performs a circular motion in a clockwise direction and a counterclockwise direction while moving in the first direction.

In some embodiments, the first direction is perpendicular to a circumferential plane formed when the radiation source performs a circular motion.

In some embodiments, the first direction forms a first included angle with a perpendicular line of a circumferential plane formed when the radiation source performs the circular motion, and the first included angle is smaller than a preset threshold.

In some embodiments, the first direction is an extension direction of a scanning bed.

In some embodiments, the controller is configured to control the radiation source to move in the first direction while performing the circular scanning motion within a scanning range, and the scanning range covers a target scanning range.

In some embodiments, the gantry comprises a base and a robotic arm assembly, the C-shaped arm is rotatably arranged at one end of the robotic arm assembly away from the base.

In some embodiments, the base is arranged on the ground or the ceiling.

In some embodiments, the scanning system is a digital subtraction angiography system.

One of the embodiments of the present disclosure provides a lift assembly for X-ray device. The lift assembly includes a shell, a driving assembly accommodated in the shell, and an arm adjustment assembly. The arm adjustment assembly moves under a driving of the driving assembly. The arm adjustment assembly includes an intermediate arm section, a target arm section, and a linkage assembly disposed between the intermediate arm section and the target arm section. The intermediate arm section can move in a first direction under the driving of the driving assembly. When the intermediate arm section moves in the first direction, the target arm section can be driven to move in the first direction by the linkage assembly. Projections of the intermediate arm section and the target arm section respectively in the first direction at least partially overlap. The target arm section is connected to a detector or a radiation source.

In some embodiments, the linkage assembly includes a first support component and a second support component arranged on the intermediate arm section, a first flexible traction component connected to the first support component, and a second flexible traction component connected to the second support component; one end of the first flexible traction component is connected to the shell, the other end of the first flexible traction component is connected to the target arm section, one end of the second flexible traction component is connected to the shell, and the other end of the second flexible traction component is connected to the target arm section.

In some embodiments, the first support component or the second support component includes a pulley or a sprocket, and the first flexible traction component or the second flexible traction component includes a rope or a chain respectively connected to the pulley or sprocket.

In some embodiments, the linkage assembly further includes a first guiding rail matched with the first sliding block, wherein the first sliding block is arranged on one of the intermediate arm section and the target arm section, and the first guiding rail is arranged on the other one of the intermediate arm section and the target arm section.

In some embodiments, the lift assembly further includes a transmission assembly disposed between the driving assembly and the intermediate arm section configured for a transmission between the driving assembly and the intermediate arm section.

In some embodiments, the transmission assembly includes a screw nut structure.

In some embodiments, the screw nut structure includes a nut rotatable relative to the shell, and a screw fixed relative to the intermediate arm section, wherein the nut is threadedly connected to the screw, and the nut is driven by the driving assembly.

In some embodiments, the lift assembly further includes a second sliding block disposed between the shell and the intermediate arm section, and a second guiding rail matched with the second sliding block, wherein the second sliding block is arranged on one of the shell and the intermediate arm section, and the second guiding rail is arranged on the other one of the shell and the intermediate arm section.

One of the embodiments of the present disclosure provides a C-shaped arm device for X-ray device, including: a supporting main body part; a C-shaped main body part connected to the supporting main body part; a detector connected to a first end of the C-shaped main body part; and a radiation source connected to a second end of the C-shaped main body part. At least one of the detector or the radiation source is connected to the C-shaped main body part through the lift assembly described above.

In some embodiments, the supporting main body part comprises a robotic arm device.

In some embodiments, a connection mode between the lift assembly and the C-shaped main body part includes a movable connection.

In some embodiments, the detector or the radiation source connected to the C-shaped main body part through the lift assembly is rotatable relative to a target arm section.

One of the embodiments of the present disclosure provides a C-shaped arm device for X-ray device, including: a supporting main body part; a C-shaped main body part connected to the supporting main body part; a detector connected to a first end of the C-shaped main body; and a radiation source connected to the second end of the C-shaped main body part. At least one of the detector or the radiation source is connected to the C-shaped main body part through a lift assembly. The lift assembly at least includes a driving assembly, a first movable part and a second movable part, and on a source image distance adjustment path defined by the detector and the radiation source. Under the driving of the driving assembly, the first movable part relative to the C-shaped main body part and the second movable part relative to the first movable part move in a same direction along the source image distance adjustment path to adjust a source image distance.

In some embodiments, the driving assembly includes a motor.

In some embodiments, the lift assembly includes a transmission assembly and the transmission assembly includes a screw nut structure.

In some embodiments, the supporting main body part includes a robotic arm assembly.

BRIEF DESCRIPTION OF THE DRAWINGS

The present disclosure is further illustrated in terms of exemplary embodiments. These exemplary embodiments are described in detail with reference to the drawings. These embodiments are not limiting, and in these embodiments, the same numbers refer to the same structures, wherein.

DETAILED DESCRIPTION

Figure 1:
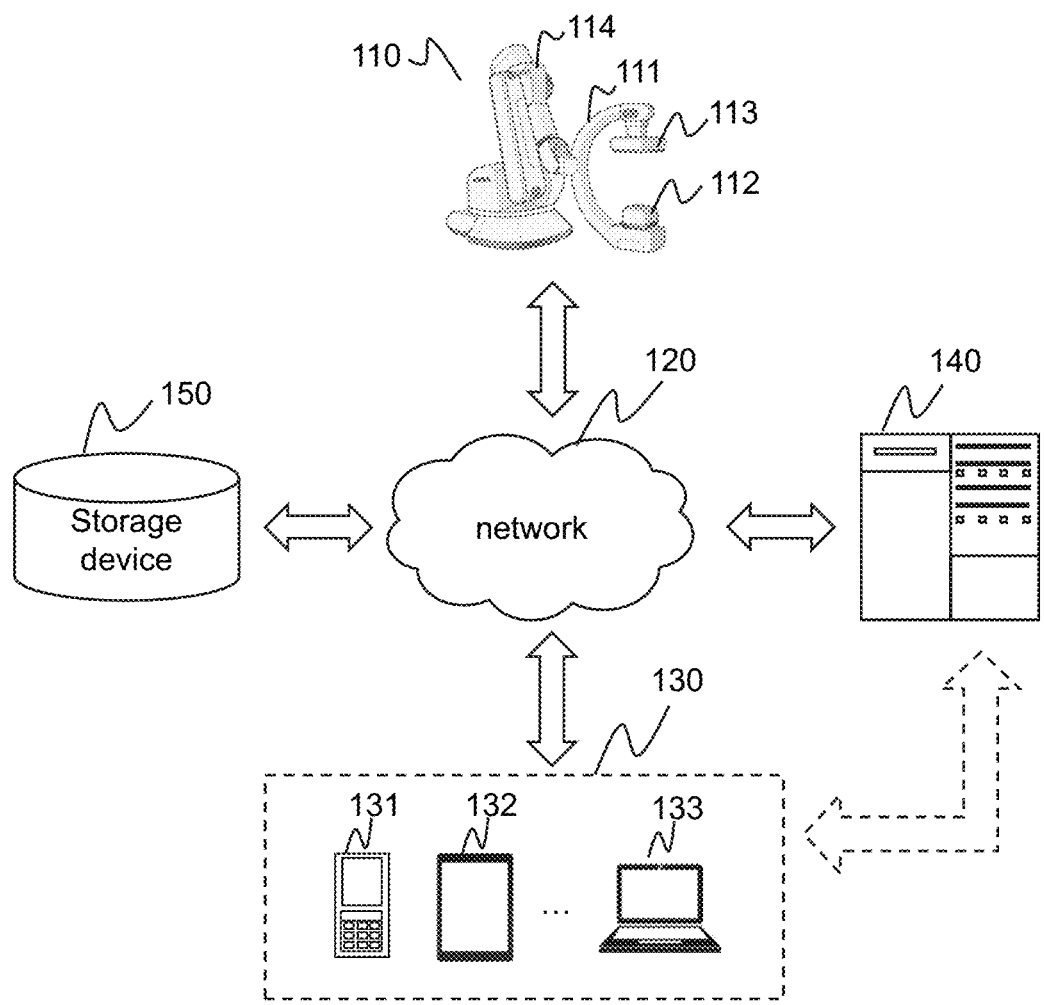
FIG. 1 is a schematic diagram illustrating an application scenario of a medical image obtaining system according to some embodiments of the present disclosure.

To illustrate the technical solutions of the embodiments of the present disclosure more clearly, the following briefly introduces the accompanying drawings that are used in the description of the embodiments. Obviously, the accompanying drawings in the following description are only some examples or embodiments of the present disclosure. For those skilled in the art, without any creative effort, the present disclosure may further be applied to other similar situations according to these drawings. Unless obviously obtained from the context or the context illustrates otherwise, the same numeral in the drawings refers to the same structure or operation.

It should be understood that "system," "device," "unit" and/or "module" as used herein is a method used to distinguish different assemblies, elements, parts, or assemblies at different levels. However, these words may be replaced by other expressions if they serve the same purpose.

As used in the disclosure and the appended claims, the singular forms "a," "an," and "the" include plural referents unless the content clearly dictates otherwise. Generally speaking, the terms "comprising" and "including" only imply that the clearly identified operations and elements are included, and these operations and elements do not constitute an exclusive list, and the method or device may further include other operations or elements.

Flowcharts are used in the present disclosure to illustrate operations performed by the system according to an embodiment of the present disclosure. It should be understood that the preceding or following operations are not necessarily performed in the exact order. Instead, the various operations may be processed in reverse order or simultaneously. At the same time, other actions may be added to these procedures, or an operation or operations may be removed from these procedures.

One of the embodiments of the present disclosure provides an image obtaining method and system. The image obtaining method disclosed in the present disclosure may be applied to a variety of medical scanning imaging devices, including but not limited to a computed radiography (CR) device, a digital radiography (DR) device, a computed tomography (CT) device, a Flat film X-ray machine, a mobile X-ray device (such as a mobile C-shaped arm machine), a digital subtraction angiography (DSA) scanner, a linear accelerator, an emission computed tomography (ECT) scanner, etc. For the purpose of illustration only, a cone-beam computed tomography (CBCT) system may be taken as an example to describe the disclosed technical solution in detail of the present disclosure, a cone-beam computed tomography (CBCT) device may refer to a mobile C-shaped arm machine or a digital subtraction angiography (DSA) scanner. It should be understood by those skilled in the art that the foregoing descriptions of CBCT is not intended to limit the scope of the present disclosure.

Figure 6:
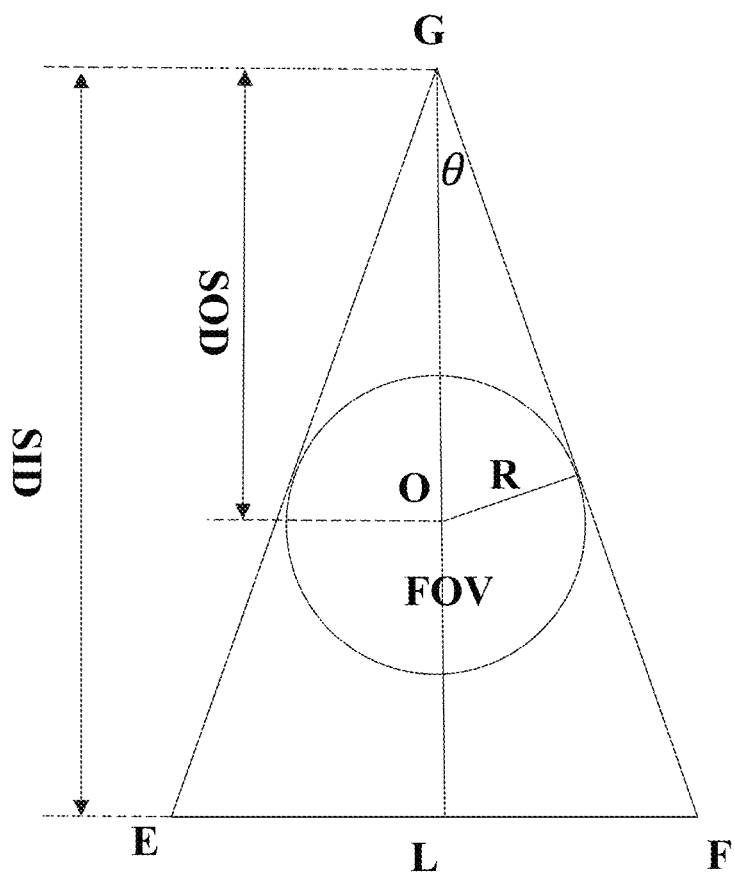
FIG. 6 is a schematic diagram illustrating a reconstruction FOV according to some embodiments of the present disclosure.

In a conventional CBCT imaging system, a size of a reconstruction field of view is limited by a size of a detector, a distance from a radiation source to the center of interest of a target object, and a distance from the source to the detector. FIG. 6 is a schematic diagram illustrating a reconstruction field of view (FOV) according to some embodiments of the present disclosure. As shown in FIG. 6, point G indicates a radiation source, EF indicates a flat panel detector, and a length of the flat panel detector is L. A center of interest of a target object is denoted as a point O, which is located on a connecting line between a geometric center point of the detector and the radiation source. SOD indicates a distance from the radiation source G to the center of interest of the target object. SID indicates a distance from the radiation source G to the detector EF. The reconstruction FOV is a circle with point O as a center and R as a radius in FIG. 6. It may be seen from FIG. 6 that a diameter of the reconstruction FOV is $2R=2\times SOD\times \sin(\theta)$, $\theta=\arctan(L/2/SID)$.

In some embodiments, the reconstruction FOV may be enlarged by translating the flat panel detector, but the translation of the flat panel detector cannot ensure that a center ray of a ray beam is perpendicular to a center point of the flat panel detector, resulting in that a filter grid is unable to filter scattered rays. Therefore, it is necessary to design a corresponding asymmetric filter grid or increase a length of the filter grid to cooperate the translation of the flat panel detector to achieve a purpose of filtering out scattered rays. In addition, for a C-shaped arm scanning apparatus (for example, a mobile C-shaped arm machine), using the translation of the flat panel detector to expand the reconstruction FOV requires not only adding a flat panel detector sliding device, but also adding a counterweight device to ensure that the center of gravity of the scanning apparatus remains unchanged. All of these may increase a manufacturing cost of the scanning apparatus. In some other embodiments, the reconstruction FOV may be enlarged by a scanning mode in which the scanning apparatus rotates a fan angle of 360°, but this scanning mode takes a long time to scan and increases a radiation dose to the target object. In some other embodiments of the present disclosure, a medical image obtaining method is provided. By deflecting the radiation source and the detector around the center point of the detector and then performing a 360° rotation scan, a larger reconstruction FOV may be obtained, and the cost of the scanning apparatus may be reduced, thereby shortening a scanning time, and reducing the radiation dose to the target object.

FIG. 1 is a schematic diagram illustrating an application scenario of a medical image obtaining system according to some embodiments of the present disclosure. In some embodiments, the medical image obtaining system may obtain scanning data of a target object based on an obtaining method disclosed in the present disclosure.

As shown in FIG. 1, a medical image obtaining system 100 may include a scanning apparatus 110, a network 120, a terminal 130, a processing device 140, and a storage device 150.

The scanning apparatus 110 may include a gantry, a radiation source 112, a detector 113, a deflection mechanism (not shown in the figure) and a rotation mechanism (not shown in the figure). The gantry may include a supporting part 111 and a robotic arm 114. The robotic arm 114 may be connected to the supporting part 111 to drive the supporting part 111 to move. The supporting part 111 may support the radiation source 112 and the detector 113. The supporting part 111 may be a C-shaped arm as shown in FIG. 1, or may be a U-shaped arm, a G-shaped arm, etc. In some embodiments, the robotic arm 114 may drive the radiation source 112 and the detector 113 to rotate together, e.g., rotate clockwise or counterclockwise around the center of interest of a target object. The radiation source 112 and the detector 113 may be arranged opposite to each other, and a space between the radiation source 112 and the detector 113 may include an accommodating space of the target object. The radiation source 112 may emit a radiation beam to the target object, and the target object may be placed in the space between the radiation source 112 and the detector 113 to be scanned. The detector 113 may detect the radiation beam (e.g., an X-ray) emitted from the radiation source 112. After receiving the radiation beam passing through the target object, the detector 113 may convert the passing radiation beam into a visible light. Then the visible light may be converted into an electrical signal through photoelectric conversion, and then be converted into digital information by an analog/digital converter, which may be input to a computing device (e.g., a computer) for processing, or be transmitted to the storage device 150 for storage. In some embodiments, the detector 113 may include one or more detector units. The detector unit may include a scintillation detector (e.g., a cesium iodide detector) and other detectors, etc. The deflection mechanism may be used to deflect the radiation source 112 and the detector 113 as a whole around a center point of the detector 113. In some embodiments, the center point of the detector 113 may refer to a geometric center point of the detector 113. For example, when the detector 113 is a flat panel detector, its center point may refer to the geometric center point of the flat panel detector. The rotation mechanism may be used to rotate the radiation source 112 and the detector 113 as a whole around a rotation center of the scanning apparatus 110 in any direction. In some embodiments, the rotation center may be a center of region of interest or a region of interest. It may be understood that the rotation center may be located on a connecting line between the radiation source 112 and the center point of the detector 113, or may be located outside the connecting line. For more descriptions of the scanning apparatus 110, please refer to FIG. 6 and related descriptions thereof.

The terminal 130 may include a mobile device 131, a tablet computer 132, a laptop computer 133, etc., or any combination thereof. In some embodiments, the terminal 130 may interact with other assemblies in the medical image obtaining system 100 over a network. For example, the terminal 130 may send one or more control instructions to the scanning apparatus 110 to control the scanning apparatus 110 to scan according to the one or more control instructions. As another example, the terminal 130 may further receive a processing result of the processing device 140, for example, a 2D image (e.g., a perspective image) and/or a 3D image (e.g., an image in reconstruction or a reconstructed image). In some embodiments, the mobile device 131 may include a smart home device, a wearable device, a mobile device, a virtual reality device, an augmented reality device, etc., or any combination thereof. In some embodiments, the smart home device may include a smart lighting device, a smart appliance control device, a smart monitoring device, a smart TV, a smart camera, a walkie-talkie, etc., or any combination thereof. In some embodiments, the wearable device may include a bracelet, a footwear, a pair of glasses, a helmet, a watch, a clothing, a backpack, a smart accessory, etc., or any combination thereof. In some embodiments, the mobile device may include a mobile phone, a personal digital assistant (PDA), a gaming device, a navigation device, a POS device, a laptop, a tablet computer, a PC, etc., or any combination thereof. In some embodiments, the virtual reality device and/or augmented reality device may include a virtual reality helmet, a virtual reality glasses, a virtual reality patch, an augmented reality helmet, a pair of augmented reality glasses, an augmented reality patch, etc., or any combination thereof. For example, the virtual reality device and/or augmented reality device may include a Google Glass™, an Oculus Rift™, a HoloLens™, or a Gear VR™, etc. In some embodiments, the terminal 130 may be a part of the processing device 140.

In some embodiments, the processing device 140 may process data and/or information obtained from the scanning apparatus 110, the terminal 130, and/or the storage device 150. For example, the processing device 140 may perform a weighting process on a part of the scanning data (e.g., the scanning data of an area that is repeatedly scanned) to determine data required for image reconstruction. As another example, the processing device 140 may perform a data pre-processing, an image reconstruction, a reconstruction post-processing, etc., on the scanning data. In some embodiments, the processing device 140 may further control a scanning action of the scanning apparatus 110. For example, the processing device 140 may control the radiation source 112 and the detector 113 to deflect a specific angle around the center point of the detector 113. As another example, the processing device 140 may control the radiation source 112 and the detector 113 to rotate and scan around the center of interest of the target object. In some embodiments, the processing device 140 may include a single server or a server group. The server group may be centralized or distributed. In some embodiments, the processing device 140 may be local or remote. For example, the processing device 140 may access information and/or data from the scanning apparatus 110, the terminal 130, and/or the storage device 150 via the network 120. As another example, the processing device 140 may be directly connected to the scanning apparatus 110, the terminal 130, and/or the storage device 150 to access information and/or data. In some embodiments, the processing device 140 may be implemented in a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data (e.g., the scanning data of the target object, etc.), an instruction, and/or any other information. In some embodiments, the storage device 150 may store data obtained from the scanning apparatus 110, the terminal 130, and/or the processing device 140. For example, the storage device 150 may store the scanning data of the target object obtained from the scanning apparatus 110. In some embodiments, the storage device 150 may store data and/or instructions performed or used by the processing device 140 to perform the exemplary methods of the present disclosure. For example, the storage device 150 may store data obtained by weighting the scanning data of the repeatedly scanned area. As another example, the storage device 150 may further store image data obtained in real-time and/or image data obtained during and/or after reconstruction. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure. For example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the medical image obtaining system 100 (e.g., the processing device 140, the terminal 130, etc.). One or more components of the medical image obtaining system 100 may access the data or instructions stored in the storage device 150 via the network 120. In some embodiments, the storage device 150 may be part of the processing device 140 or may be separate and connected directly or indirectly to the processing device 140.

The network 120 may include any suitable network that can facilitate the exchange of information and/or data for the medical image obtaining system 100. The network 120 may further be part of a hospital network such as, a Hospital Information System (HIS) or a Picture archiving and communication system (PACS), or a part of the other hospital networks, or a network separated from and connected to the HIS, the PACS, or the other hospital networks. In some embodiments, one or more components of the medical image obtaining system 100 (e.g., the scanning apparatus 110, the terminal 130, the processing device 140, the storage device 150, etc.) may communicate information and/or data with one or more other components of the medical image obtaining system 100 via the network 120. For example, the processing device 140 may obtain plan data from a data processing planning system via the network 120. In some embodiments, the network 120 may be or include a public network (e.g., the Internet), a private network (e.g., a local area network (LAN), a wide area network (WAN)), a wired network (e.g., an Ethernet network), a wireless network (e.g., an 802.11 network, a Wi-Fi network, etc.), a cellular network (e.g., a Long Term Evolution (LTE) network), a gantry relay network, a virtual private network (VPN), a satellite network, a telephone network, routers, hubs, switches, server computers, or the like, or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the medical image obtaining system 100 may be connected to the network 120 to exchange data and/or information.

Figure 2:
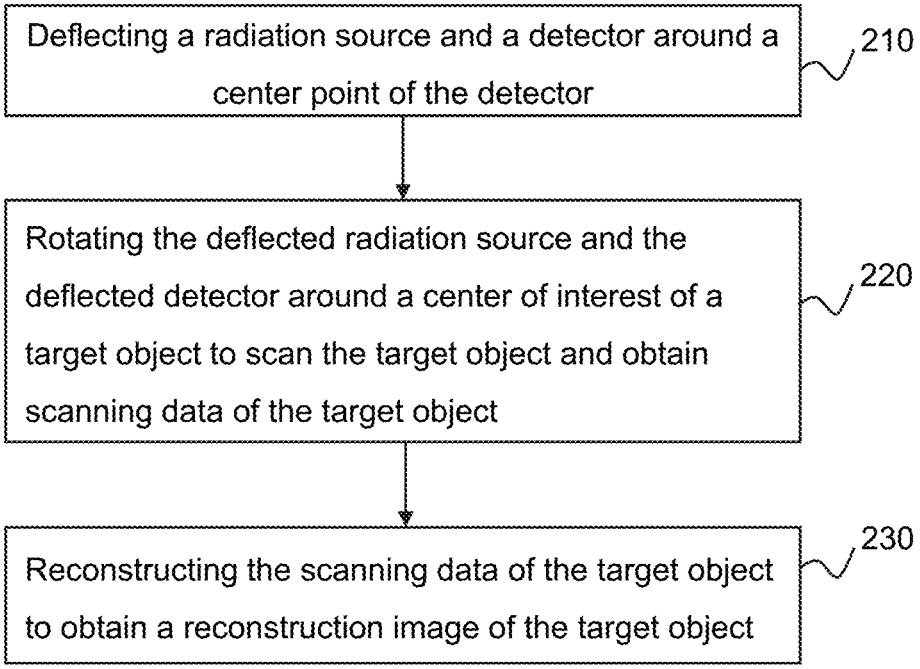
FIG. 2 is an exemplary flowchart illustrating an exemplary method for obtaining a medical image according to some embodiments of the present disclosure.

FIG. 2 is a flowchart illustrating an exemplary medical image obtaining method according to some embodiments of the present disclosure. In some embodiments, a process 200 may be performed by a processing logic, including a hardware (e.g., a circuit, a dedicated logic, a programmable logic, a microcode, etc.), a software (an instruction run on a processing device to perform hardware simulation), etc., or any combination thereof. One or more operations in the process 200 for obtaining a medical image shown in FIG. 2 may be implemented by the processing device 140 shown in FIG. 1. For example, the process 200 may be stored in the storage device 150 in the form of an instruction and may be retrieved and/or executed by the processing device 140.

As shown in FIG. 2, the medical image obtaining method may include the following operations.

In 210, a radiation source and a detector may be deflected around a center point of the detector. The operation 210 may be performed by a deflection module 510.

The medical image obtaining method of the present disclosure may be implemented by a CBCT system. In some embodiments, the CBCT system may include but be not limited to, a mobile C-shaped arm machine or a DSA scanner. Further, in some examples, the DSA scanner may be a robotic DSA scanner, i.e., the aforementioned radiation source and detector may be supported by a C-shaped arm, which is handled by a robot. The CBCT system may include a radiation source and a detector. The radiation source may emit a radiation beam (e.g., an X-ray) that passes through a target object and is attenuated. The detector may be set opposite to the radiation source. The detector may receive the radiation beam (for example, the X-ray) passing through the target object, and convert it into a visible light. The visible light may be converted into an electrical signal through photoelectric conversion. Then the detector may convert the electrical signal into digital information by an analog/digital converter. In some embodiments, the detector may include but be not limited to, a flat panel detector. For the convenience of description, in the present disclosure, the DSA scanner may be taken as an example to illustrate the medical image obtaining method and system.

Figure 3:
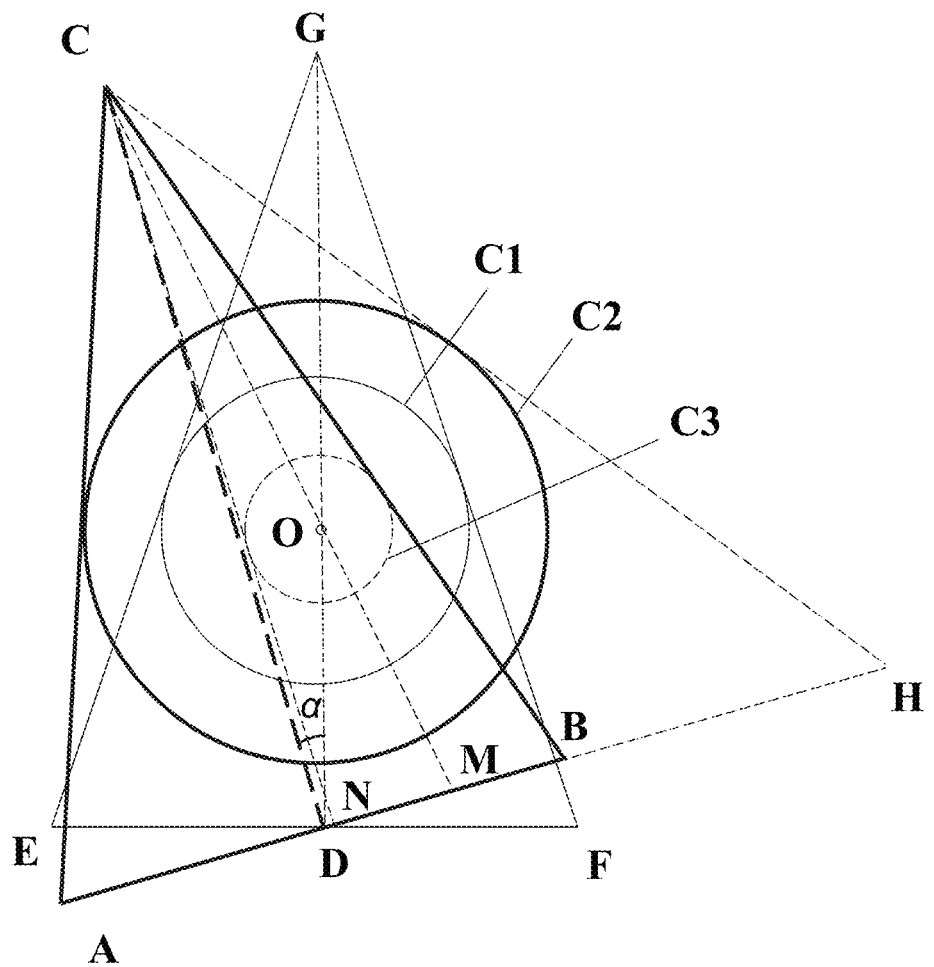
FIG. 3 is a schematic diagram illustrating a first reconstruction field of view and a second reconstruction FOV obtained through methods for obtaining a medical image according to some embodiments of the present disclosure.

In some embodiments, the center point of the detector may refer to a geometric center point of the detector. For example, when the detector is a flat panel detector, its center point may refer to the geometric center point of the flat panel detector. In the present disclosure, when scanning, the processing device 140 may first deflect the radiation source and the detector around the center point of the detector. As shown in FIG. 3, D is a geometric center point of the detector, G is a position of the radiation source before the deflection, EF is a position of the detector before the deflection, C is a position of the radiation source after the deflection, and AB is a position of the detector after the deflection. A deflection direction may include a clockwise deflection direction or a counterclockwise deflection direction. A deflection angle may make a scanning view of a single gantry (e.g., an area enclosed by triangle ABC) after the deflection include a center of interest of the target object, so that the scanning view of the single gantry may cover more than half of a second reconstruction FOV (e.g., an area enclosed by a larger ring). In this embodiment, a rotation center may be aligned with the treatment or imaging iso-center (e.g., a center of an area to be imaged) of the DSA scanner, which is located outside line CD connecting the radiation source and the center of the detector. In some embodiments, the deflection angle of the deflection is adjustable. In some embodiments, there may be different deflection angles according to different usage requirements. For example, when a volume of the target object is relatively large, the deflection angle may be increased accordingly. In some embodiments, the deflection angle may be in a range of 1°~60°. For example, the deflection angle may include but be not limited to, 1°, 3°, 5°, 10°, 30°, 45°, 60°, etc. In some embodiments, the deflection angle may be the smallest angle for the second reconstruction FOV to cover the target object. For more descriptions about the scanning view of the single gantry and the second reconstruction FOV, please refer to the relevant descriptions of operation 220 and FIG. 3 of the present disclosure, which are not repeated here.

In 220, the deflected radiation source and the deflected detector may be rotated around a center of interest of a target object (or a rotation center of the DSA scanner before the deflection) to scan the target object and obtain scanning data of the target object. Operation 220 may be performed by a rotation module 520.

In some embodiments, the target object may include a patient, other medical experimental objects (e.g., an animal such as an experimental mouse), organs and/or tissues (e.g., an arm, etc.) of a patient, a phantom, or other medical experimental objects, etc. For the definition of the rotation center, please refer to the relevant descriptions in operation 210. The processing device 140 may rotate the deflected radiation source and the deflected detector around the center of interest of the target object to scan the target object. In some embodiments, the rotation direction may be any direction centered on the center of interest of the target object. For example, a clockwise direction, a counterclockwise direction, etc. The rotation angle may include 10°, 15°, 90°, 180°, or 360°, etc.

In some embodiments, a reconstruction FOV may refer to the largest circular area with the center of interest of the target object as the center that can be covered by ray beams formed by a rotation of the scanning apparatus in a specific angle range. Circle C1 in FIG. 3 may denote a first reconstruction FOV, which can be understood as the reconstruction FOV of the scanning apparatus rotating for 360° before the radiation source and the detector are deflected. A second reconstruction FOV may include a reconstruction FOV of the scanning apparatus rotating for 360° after the radiation source and the detector are deflected, e.g., the largest circular area C2 in FIG. 3. It can be seen intuitively from FIG. 3 that the second reconstruction FOV circle C2 is larger than the first reconstruction FOV circle C1. For more descriptions about the first reconstruction FOV and the second reconstruction FOV, please refer to FIG. 3 of the present disclosure and related descriptions thereof, which are not repeated here.

After the scanning apparatus rotates and scans, the processing device 140 may obtain scanning data of the target object from the detector 113 and/or the storage device 150.

In 230, reconstructing the scanning data of the target object to obtain a reconstruction image of the target object. Operation 230 may be performed by a reconstruction module 530.

In some embodiments, the reconstruction may include obtaining the reconstruction image of the target object based on the scanning data of the target object using, for example, an iterative reconstruction algorithm. Exemplary iterative reconstruction algorithms may include a simultaneous algebraic reconstruction technique (SART), a simultaneous iterative reconstruction technique (SIRT), an ordered subset convex (OSC) technique, an ordered subset maximum likelihood technique, an ordered subset expectation maximization (OSEM) technique, an adaptive statistical iterative reconstruction (ASIR) technique, a least squares QR method, an expectation maximization (EM) technique, an ordered subset-separable parabolic substitution (OS-SPS) technique, an algebraic reconstruction technique (ART), a Kacsmarz reconstruction technique, or any other iterative reconstruction technique that meets specific application requirements. In some embodiments, the reconstruction may further include obtaining the reconstruction image of the target object based on the scanning data of the target object using a direct back projection technique. In some embodiments, the reconstruction may further include using an analytical technique to obtain the reconstruction image of the target object based on the scanning data of the target object. Exemplary analytical technique may include a Fourier transform reconstruction technique and a filtered back projection technique.

Due to the deflection of the radiation source and the detector, during the process of rotating 360° around the center of interest of the target object, part of the target object may always be scanned, that is, the scanning data of part of the target object may be repeatedly scanned for twice or more. In other words, during the 360° rotation of the radiation source and the detector around the center of interest of the target object, some areas may not be scanned again after the radiation source and the detector rotate more than 180° around the center of interest of the target object, while some areas may always be scanned during the 360° rotation of the radiation source and the detector around the center of interest of the target object. The area that can always be scanned may be referred to as a repeatedly scanned area. Obvious artifacts may be generated when using the scanning data of the repeatedly scanned area for the image reconstruction. Therefore, the scanning data of the repeatedly scanned area needs to be processed before reconstruction to obtain "de-duplicated" scanning data which can be used to reconstruct the reconstruction image with better image quality. In some embodiments, the processing the scanning data may include weighting the scanning data based on a preset weight curve. The weighting may refer to multiplying the scanning data of the repeatedly scanned area by different weight coefficients to eliminate an influence of the scanning data of the repeatedly scanned area on the reconstruction image. For more descriptions of the preset weight curve, please refer to FIG. 4 and related descriptions, which are not repeated here.

It should be noted that the above descriptions about the process 200 is merely for example and illustration, and does not intend to limit the scope of the present disclosure. For persons having ordinary skills in the art, multiple modifications and variations may be made to the process 200 under the teachings of the present disclosure. However, those variations and modifications do not depart from the scope of the present disclosure.

FIG. 3 is a schematic diagram illustrating a first reconstruction FOV and a second reconstruction FOV obtained through a medical image obtaining method according to some embodiments of the present disclosure.

As shown in FIG. 3, triangle EFG indicates a positional relationship between the radiation source and the detector before the deflection. Triangle ABC indicates the positional relationship between the radiation source and the detector after the deflection. A center of interest of a target object before and after the deflection of the radiation source and the detector is point O, and point O is located on a connection line between a geometric center point of the detector and a focal point of the radiation source before the deflection. In triangle EFG, EF represents a position of a flat panel detector before the deflection, point D represents the center point of the flat panel detector, and point G represents the focal point of the radiation source before the deflection. Circle C1 represents a reconstruction FOV (the first reconstruction FOV) before the radiation source and the detector are deflected. After the radiation source and the detector (the triangle EFG in FIG. 3) are deflected by a specific angle (such as a deflection angle α) around the center point D of the detector, a schematic diagram (i.e., triangle ABC) of the positional relationship after the deflection is obtained.

In the triangle ABC, AB represents a position of the deflected flat panel detector, point D remains unchanged and still represents the center point of the flat panel detector, and point C represents the focal point of the deflected radiation source. Circle C2 represents a reconstruction FOV (the second reconstruction FOV) after the radiation source and the detector are deflected. It can be seen from FIG. 3 that the reconstruction FOV (the second reconstruction FOV) after the deflection of the radiation source and the detector is larger than the reconstruction FOV (the first reconstruction FOV) before the deflection of the radiation source and the detector. And if the radiation source and the detector are not deflected, to obtain the second reconstruction FOV as shown in FIG. 3, a detector with a size equivalent to a size of AH in FIG. 3 is required. It may be seen that using the medical image obtaining method described in the present disclosure, a larger reconstruction FOV may be obtained without increasing the size of the detector. In some embodiments, the BH shown in FIG. 3 may be viewed as a length of a "virtual detector". The virtual detector refers to a part of a detector (e.g., AH in FIG. 3) beyond the actual detector (e.g., AB in FIG. 3) required to achieve the same size of FOV (e.g., the second reconstruction FOV) without deflection.

In some embodiments, a scanning view of a single gantry may refer to a scanning view corresponding to a certain rotation angle when the radiation source and the detector rotate around the center of interest of the target object. As shown in FIG. 3, the area enclosed by triangle ABC may be taken as a scanning view of a single gantry. In some embodiments, the magnitude of the deflection angle (such as the deflection angle α) should ensure that boundary rays AC and BC do not cross the center of interest of the target object point O (as shown in the figure, when point C is deflected to the right around point D, and AC does not cross point O; and similarly, when point C is deflected to the left around point D, BC cannot cross point O). As can be seen in FIG. 3, according to this condition, the scanning view of the single gantry after deflecting the radiation source and the detector may cover more than half of the second reconstruction FOV to ensure the acquisition of sufficient scanning data. In some embodiments, the deflection angle is adjustable. In some embodiments, there may be different deflection angles according to different usage requirements. For example, when the volume of the target object is relatively large, the deflection angle may be increased accordingly. In some embodiments, the deflection angle may be in a range of 1°~60°. For example, the deflection angle may include but be not limited to, 1°, 3°, 5°, 10°, 30°, 45°, 60°, etc. In some embodiments, the deflection angle may be the smallest angle for the second reconstruction FOV to cover the target object. For example, when the minimum deflection angle required for the second reconstruction FOV to cover the target object (e.g., an abdomen) is 30°, the deflection angle may be set to 30°. By setting the deflection angle as the minimum angle for the second reconstruction FOV to cover the target object, an image reconstruction quality may be effectively improved under the condition of sufficient reconstruction area.

Figure 4:
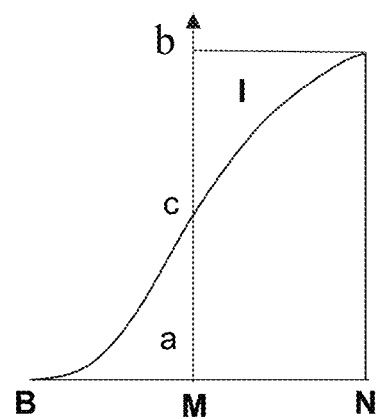
FIG. 4 is a schematic diagram illustrating a preset weight curve according to some embodiments of the present disclosure.

FIG. 4 is a schematic diagram illustrating a preset weight curve according to some embodiments of the present disclosure.

For more descriptions of a repeatedly scanned area, please refer to the relevant descriptions of operation 230 of the present disclosure. It can be understood that the repeatedly scanned area may be the area enclosed by circle C3 shown in FIG. 3. A preset weight curve is related to positions at the detector corresponding to the repeatedly scanned area. In some embodiments, positions at the detector corresponding to the repeatedly scanned area may include positions at the detector where scanning data of the repeatedly scanned area is collected. For example, the positions at the detector corresponding to the repeatedly scanned area may be positions within the BN part of the detector shown in FIG. 3. Specifically, as shown in FIG. 3, starting from the deflected radiation source C, two tangent lines CB and CN tangent to the repeatedly scanned area (the circle C3) may be determined. The tangent lines CB and CN respectively pass through a first point (point B) and a second point (point N) of the deflected detector AB. Positions between the first point (point B) and the second point (point N) on the detector may be used as positions at the detector corresponding to the repeatedly scanned area.

Referring to FIG. 3, when determining the preset weight curve, a straight-line CO starting from the deflected radiation source C and passing through the center O of interest of the target object needs to be determined. The straight-line CO passes through a third point (point M) of the deflected detector AB. It can be seen from FIG. 3 that the first point (point B) may be located at an edge of the deflected detector AB, the second point (point N) may be located in a non-edge area of the deflected detector AB, and the third point (point M) may be located between the first point (point B) and the second point (point N).

The preset weight curve may be determined by: setting a weight of the scanning data corresponding to the first point (e.g., point B) as a; setting a weight of the scanning data corresponding to the second point (e.g., point N) as b; setting a weight of the scanning data corresponding to the third point (e.g., point M) as c, wherein $0 \le a < c < b \le 1$. Then, the first point (e.g., point B), the third point (e.g., point M), and the second point (e.g., point N) may be sequentially connected by a smooth curve, and the smooth curve may be used as the preset weight curve. In some embodiments, the smooth curve passing through the first point (e.g., point B), the third point (e.g., point M), and the second point (e.g., point N) may be a type of curve distribution. For example, the smooth curve passing through the first point (e.g., point B), the third point (e.g., point M), and the second point (e.g., point N) may include a sine curve, a cosine curve, a tangent curve, or a logarithmic curve, etc. In some embodiments, the smooth curve passing through the first point (e.g., point B) and the third point (e.g., point M) may be of one type of curve distribution, the smooth curve passing through the third point (e.g., point M) and the second point (e.g., point N) may be the other type of curve distribution. For example, the smooth curve passing through the first point (e.g., point B) and the third point (e.g., point M) may be a sine curve, and the smooth curve passing through the third point (e.g., point M) and the second point (e.g., point N) may be a logarithmic curve. As another example, the smooth curve passing through the first point (e.g., point B) and the third point (e.g., point M) may be a logarithmic curve, and the smooth curve passing through the third point (e.g., point M) and the second point (e.g., point N) may be a tangent curve. The present disclosure does not make any limitation on the type of the smooth curve.

As shown in FIG. 4, the abscissa indicates the position at the detector that collects the scanning data of the repeatedly scanned area, and the ordinate indicates a weight value. In FIG. 4, a smooth curve I connecting the weight value (a) corresponding to the first point (point B) to the weight value (c) corresponding to the third point (e.g., point M), and then to the weight value (b) corresponding to the second point (point N) may be determined as the preset weight curve. Other points on the preset weight curve may respectively correspond to weight values of other parts of the repeatedly scanned area. Specifically, for the scanning data of each gantry of the repeatedly scanned area, the positions at the detector that collect the scanning data of the repeatedly scanned area may be obtained. The weight values corresponding to the positions at the detector that collects the scanning data of the repeatedly scanned area may be determined based on the positions at the detector and the preset weight curve. The "de-duplicated" scanning data may be obtained by multiplying the scanning data of the repeatedly scanned area by the weight values so as to reconstruct and obtain a reconstruction image with better image quality.

It should be noted that the above descriptions about the preset weight curve and its determination mode in FIG. 4 are merely for example and illustration, and does not intend to limit the scope of the present disclosure. For persons having ordinary skills in the art, multiple modifications and variations may be made to the preset weight curve and its determination mode under the teachings of the present disclosure. However, those variations and modifications do not depart from the scope of the present disclosure.

Figure 5:
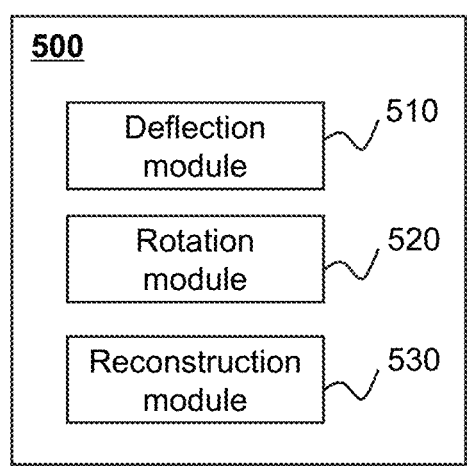
FIG. 5 is a block diagram illustrating a system for obtaining a medical image according to some embodiments of the present disclosure.

FIG. 5 is a block diagram illustrating a system for obtaining a medical image according to some embodiments of the present disclosure.

As shown in FIG. 5, a medical image obtaining system 500 may include a deflection module 510 and a rotation module 520. In some embodiments, the deflection module 510 may be configured to deflect a radiation source and a detector around a center of interest of a target object. In some embodiments, the rotation module 520 may be configured to rotate the deflected radiation source and the deflected detector around the center of interest of the target object to scan the target object and obtain scanning data of the target object. In some embodiments, the medical image obtaining system 500 may further include a reconstruction module 530. The reconstruction module 530 may be configured to reconstruct the scanning data of the target object to obtain a reconstruction image of the target object. If the radiation source and the detector have a first reconstruction FOV before the deflection, and have a second reconstruction FOV after the deflection, the second reconstruction FOV is larger than the first reconstruction FOV. For detailed descriptions of the deflection module 510, the rotation module 520, and the reconstruction module 530, please refer to FIG. 2 of the present disclosure and the related descriptions thereof, which are not repeated here.

It should be understood that for those skilled in the art, after understanding the principle of the system, various modules may be combined arbitrarily, or a sub-system may be formed to connect with other modules without departing from the principle. For example, the deflection module 510 and the rotation module 520 disclosed in FIG. 5 may be one module to implement the functions of the above two modules. As another example, the modules may share one storage module, or each module may further have its own storage module. Such deformations are all within the protection scope of the present disclosure.

The present disclosure further provides a cone-beam computed tomography (CBCT) scanner. As shown in FIG. 1, the cone-beam computed tomography scanning apparatus (or referred to as the scanning apparatus 110) may include a robotic arm 114, a radiation source 112, and a detector 113. The cone-beam computed tomography scanning apparatus (or the scanning apparatus 110) may further include a supporting part 111 (e.g., a C-shaped arm). The robotic arm 114 may be connected to the supporting part 111 to drive the supporting part 111 to move. The supporting part 111 may be configured to support the radiation source 112 and the detector 113. A space between the radiation source 112 and the detector 113 may include an accommodation space for the target object. The radiation source 112 may be configured to emit X-rays that pass through the target object and are attenuated. The detector 113 may be set opposite to the radiation source 112. The detector 113 may receive X-rays passing through the target object, convert the X-rays into a visible light, and convert the visible light into an electrical signal through photoelectric conversion. Then the electrical signal may be converted into digital information by an analog/digital converter.

The robotic arm 114 of the cone-beam computed tomography scanner (or the scanning apparatus 110) may have a deflection mode and a rotation mode. In some embodiments, the robotic arm 114 may further have a translation mode, such as a left and right translation mode. In some embodiments, the robotic arm 114 may further have a lifting mode, such as an upward and downward lifting mode. In some embodiments, the robotic arm 114 may further have a combined translation-lifting mode, such as a mode in which the robotic arm 114 translates to right and then descends.

In the deflection mode, the robotic arm 114 may drive the radiation source 112 and the detector 113 to deflect around the center point of the detector 113. In some embodiments, the center point of the detector 113 may refer to a geometric center point of the detector 113. For example, if the detector 113 is a flat panel detector, its center point may refer to the geometric center point of the flat panel detector.

In the rotation mode, the robotic arm 114 may drive the deflected radiation source 112 and the deflected detector 113 to rotate around the center of interest of the target object so as to scan the target object and obtain scanning data of the target object. In some embodiments, the rotation direction may be any direction centered on the center of interest of the target object. For example, a clockwise direction, a counterclockwise direction, etc. The rotation angle may include 10°, 15°, 90°, 180°, or 360°, etc.

Assuming that the radiation source and the detector have a first reconstruction FOV before the deflection and a second reconstruction FOV after the deflection. Then the second reconstruction FOV is larger than the first reconstruction FOV. For detailed descriptions of the first reconstruction FOV and the second reconstruction FOV, please refer to FIG. 2, FIG. 3, and the related descriptions of the present disclosure, which are not repeated here.

In some embodiments, the cone-beam computed tomography scanner may include a digital subtraction angiography (DSA) scanner or a mobile C-shaped arm machine. In some embodiments, the robotic arm 114 may be replaced by a robot. The robot may be a KUKA robot or a multi-degree-of-freedom robot, which may include an executing part, a driving part, a controlling part, etc. In some embodiments, the controlling part may control the driving part based on an instruction (e.g., a control instruction from a processing device) to drive the executing part to perform the abovementioned deflection mode and rotation mode. For example, the controlling part may include a controller, a microcontroller unit (MCU), a reduced instruction set computer (RISC), etc. In some embodiments, the driving part may be configured to drive the executing part to execute the aforementioned deflection mode and rotation mode. For example, the driving part may include a motor, etc. In some embodiments, the executing part may execute the aforementioned deflection mode and rotation mode. For example, the executing part may include a deflection-rotation mechanism, one end of the deflection-rotation mechanism may be connected to the supporting part 111, and the other end of the deflection-rotation mechanism may be connected to the driving part. As an example, in the deflection mode, the controlling part may control the driving part, the driving part may drive the executing part, and the executing part may deflect the radiation source 112 and the detector 113 around the center point of the detector 113. In the rotation mode, the controlling part may control the driving part, the driving part may drive the executing part, and the executing part may make the deflected radiation source 112 and the deflected detector 113 rotate around the center of interest of the target object to scan the target object and obtain the scanning data of the target object.

The present disclosure further provides a cone-beam computed tomography scanning apparatus, as shown in FIG. 1, the scanning apparatus 110 may include the cone-beam computed tomography scanning apparatus (CBCT). The cone-beam computed tomography device may include a gantry, a radiation source 112, and a detector 113. The gantry may include a supporting part 111. The supporting part 111 may be configured to support the radiation source 112 and the detector 113. A space between the radiation source 112 and the detector 113 may include an accommodation space for a target object. The radiation source 112 may be configured to emit X-rays that passes through the target object and are attenuated. The detector 113 may be set opposite to the radiation source 112. The detector 113 may receive the X-rays passing through the target object, convert the X-rays into a visible light, and convert the visible light into an electrical signal through photoelectric conversion. The electrical signal may be converted into digital information by an analog/digital converter.

The cone-beam computed tomography device (CBCT) may further include a deflection mechanism (not shown in the figure) configured to deflect the radiation source 112 and the detector 113 around a center point of the detector 113. In some embodiments, the center point of the detector 113 may refer to a geometric center point of the detector 113. For example, if the detector 113 is a flat panel detector, its center point may be the geometric center point of the flat panel detector. In some embodiments, the deflection mechanism may include a first power device and a deflection shaft. One end of the deflection shaft may be connected to the first power device, and the other end of the deflection shaft may be connected to the radiation source 112 and the detector 113 (or the supporting part 111). The first power device may be configured to provide a deflection power to the deflection shaft so as to deflect the radiation source 112 and the detector 113 around the center point of the detector 113. In some embodiments, the first power device may include an electric motor, etc. The present disclosure does not make any limitation on the deflection mechanism, as long as any electro-mechanical structure that can drive the radiation source and the detector as a whole to deflect around the center point of the detector may be used to achieve the technical purpose of the present disclosure.

In some embodiments, the cone-beam computed tomography device (CBCT) may further include a first control mechanism. The first control mechanism may control a deflection angle of the radiation source 112 and the detector 113 based on a scanning protocol. In some embodiments, a scanning view of a single gantry after the deflection of the radiation source and the detector covers at least half of the second reconstruction FOV. For more descriptions about the scanning view and the second reconstruction FOV of the single gantry, please refer to FIG. 2, FIG. 3, and the related descriptions.

The cone-beam computed tomography device (CBCT) may further include a rotation mechanism (not shown in the figure). The rotation mechanism may be configured to rotate the deflected radiation source 112 and the deflected detector 113 around the center of interest of the target object. In some embodiments, the rotation mechanism may include a second power device and a rotation shaft. One end of the rotation shaft may be connected to the second power device, and the other end of the rotation shaft may be connected to the gantry (e.g., the supporting part 111). The second power device may be configured to provide a power for rotating the rotation shaft so as to drive the radiation source 112 and the detector 113 to rotate around the center of interest of the target object. In some embodiments, the second power device may include an electric motor, etc. The disclosure does not make any limitation on the rotation mechanism, as long as any electro-mechanical structure that can drive the deflected radiation source and the deflected detector to rotate around the center of interest of the target object as a whole may be used to achieve the technical purpose of the present disclosure. Assuming that the radiation source and the detector have a first reconstruction FOV before the deflection and a second reconstruction FOV after the deflection, the second reconstruction FOV is larger than the first reconstruction FOV. For detailed descriptions of the first reconstruction FOV and the second reconstruction FOV, please refer to FIG. 2, FIG. 3, and the related descriptions of the present disclosure, which are not repeated here.

In some embodiments, the cone-beam computed tomography device (CBCT) may further include a second control mechanism. The second control mechanism may be configured to control the radiation source 112 and the detector 113 to rotate around the center of interest of the target object to scan the target object and obtain scanning data of the target object.

In some embodiments, the functions of the deflection mechanism and the rotation mechanism of the cone-beam computed tomography device (CBCT) may be implemented by one mechanism (e.g., a deflection-rotation mechanism). Any electro-mechanical structure that can deflect the radiation source and detector around the center point of the detector and rotate the deflected radiation source and the deflected detector around the center of interest of the target object to scan the target object may be used to achieve the technical purpose of the present disclosure, which is not limited in the present disclosure.

The beneficial effects of the medical image obtaining method and system according to the embodiments of the present disclosure may include but be not limited to: (1) a relatively large reconstruction FOV may be obtained with a certain size of the detector; (2) the "de-duplicated" scanning data may be obtained by weighting the scanning data of the repeatedly scanned area based on the obtained reconstruction FOV, which can be reconstructed to obtain an image with no artifact and better quality; (3) the scanning apparatus may have a compact structure, which is more convenient for a clinical operation.

Figure 7:
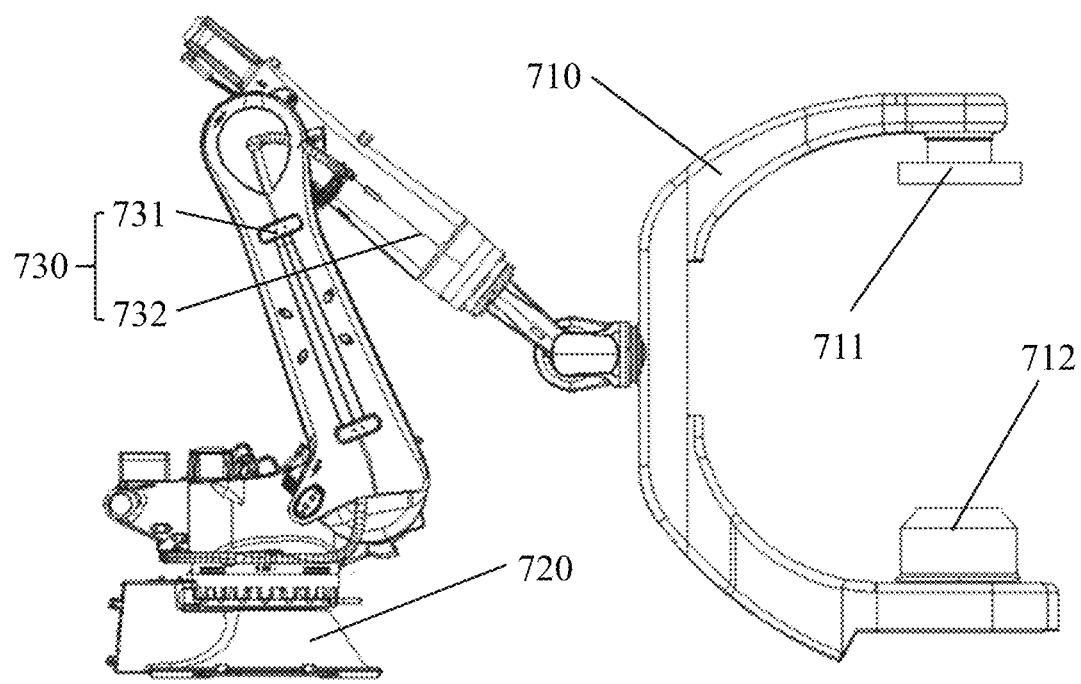
FIG. 7 is a schematic structural diagram illustrating a scanning system based on a C-shaped arm according to some embodiments of the present disclosure.
Figure 8:
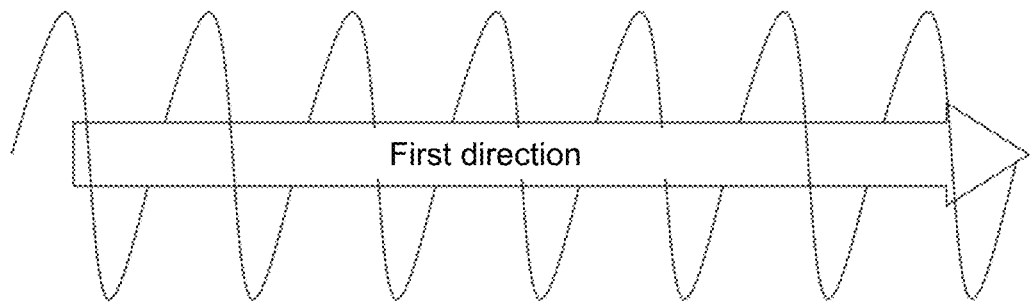
FIG. 8 is a schematic diagram illustrating a motion trajectory of a radiation source according to some embodiments of the present disclosure.
Figure 9:
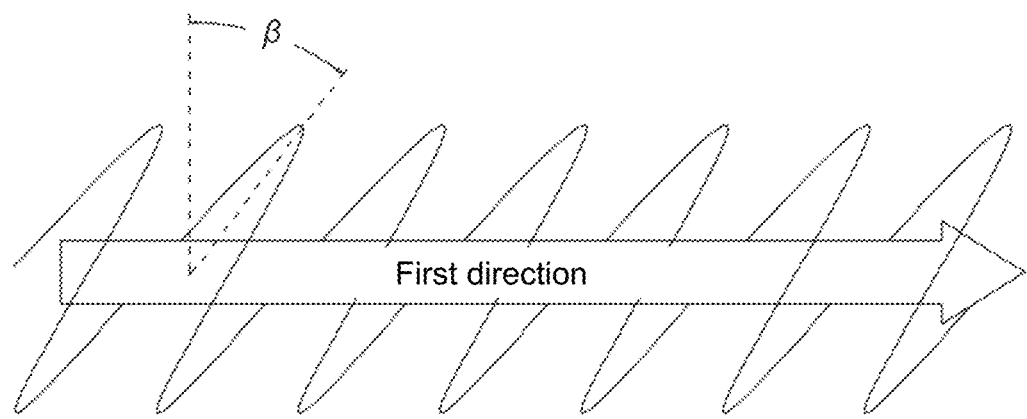
FIG. 9 is a schematic diagram illustrating a motion trajectory of a radiation source according to some other embodiments of the present disclosure.

One of the embodiments of the present disclosure provides a scanning system (or a scanning apparatus) based on a C-shaped arm. FIG. 7 is a schematic structural diagram illustrating a scanning system based on a C-shaped arm according to some embodiments of the present disclosure. FIG. 8 is a schematic diagram illustrating a motion trajectory of a radiation source according to some embodiments of the present disclosure. FIG. 9 is a schematic diagram illustrating a motion trajectory of a radiation source according to some other embodiments of the present disclosure. The scanning system based on the C-shaped arm according to some embodiments of the present disclosure is described in detail as follows with reference to FIGS. 7 to 9. It should be noted that the following embodiments are only used to explain the present disclosure, and do not limit the present disclosure.

In some embodiments of the present disclosure, as shown in FIG. 7, a C-shaped arm-based scanning system 700 may include a gantry, a controller, a C-shaped arm 710, a ray detector 711 (or be referred to as a detector), and a radiation source 712. The ray detector 711 and the radiation source 712 may be set on both ends of the C-shaped arm 710. The C-shaped arm 710 may be connected to the gantry. The controller may be configured to control a motion of the gantry to drive the C-shaped arm 710 to move. It should be understood that the movement of the C-shaped arm 710 driven by the gantry may not only include rotation or translation, but also include a compound motion. It should be noted that the radiation source 712 may be regarded as a device capable of emitting a ray (an X-ray, a y ray, or an electron ray, etc.), and the ray detector 711 may be regarded as a device capable of receiving the ray emitted by the radiation source 712. Through a cooperation of the radiation source 712 and the ray detector 711, operations such as a medical examination or treatment may be implemented.

In some embodiments, the controller may be disposed in the C-shaped arm 710 or in the gantry. In some embodiments, the aforementioned controller may also be an independent device, and has a signal connection (e.g., an electrical connection, a wireless connection, etc.) with the gantry. It should be noted that the controller may be implemented by a hardware, a software, or a combination thereof. The hardware part may be implemented by using a dedicated logic and the software part may be stored in a memory and executed by a suitable instruction execution system, such as a microprocessor or a specially designed hardware. Those skilled in the art may be noted that the methods and systems described above may be implemented using a computer-executable instruction and/or may be through a control code embodied in processor, for example, on a carrier medium such as a hard disk, a magnetic disk, a CD, or a DVD-ROM, or such code is provided on a programmable memory of a ROM (firmware) or a data carrier such as an optical or electronic signal carrier. The controller of the present disclosure may not only be implemented by VLSIs or gate arrays, semiconductors such as logic chips, transistors, etc., or hardware circuits of programmable hardware devices such as field programmable gate arrays, programmable logic devices, etc., but also may be implemented by, for example, software executed by various types of processors, and may further be implemented by a combination of the above-described hardware circuits and software (e.g., firmware).

In some embodiments, the controller may control the gantry to drive the C-shaped arm 710 to perform a circular scan. An exposure range formed by rays emitted by the radiation source 712 and received by the ray detector 711 is a cone-beam. When reconstructing using projection images obtained through scanning using the cone-beam, a sufficient data condition of the projection data is that each plane intersecting with the object contains at least one focal point position of the cone-beam (e.g., the position of the radiation source 712). Therefore, in the embodiments in which the C-shaped arm 710 only performs the circular scan, the data obtained by scanning does not satisfy the sufficient data condition. Even with a 360° circular scan, only a middle slice may satisfy the sufficient data condition, and other slices do not satisfy the sufficient data condition. Due to a serious lack of data, a scan that does not satisfy the sufficient data condition may lead to a poor quality of the reconstruction image, which cannot meet the needs of clinicians for diagnosis.

To improve the image quality of the reconstruction image and increase the scanning range of the patient, in this embodiment, the controller may control the gantry to drive the C-shaped arm 710, so that the radiation source 712 at one end of the C-shaped arm 710 can move in a first direction while performing the circular scanning motion.

In some embodiments, the controller may control the C-shaped arm 710 to move along a motion trajectory shown in FIG. 8. A curve in FIG. 8 represents the motion trajectory formed when the radiation source 712 (or the detector) is driven by the C-shaped arm 710 to move in the first direction while performing the circular motion, that is, the radiation source 712 may scan along a spiral trajectory. The radiation source 712 and the ray detector 711 may expand the exposure range through the spiral trajectory formed by the superposition of the linear motion in the first direction and the circular motion. Through the spiral scanning, the spiral trajectory of the radiation source 712 may intersect with any plane passing through the object, and the scan in this manner can satisfy the sufficient data condition. Compared with a traditional scanning manner, an image with a higher image quality may be acquired.

In some embodiments, under the control of the controller, the radiation source 712 can scan along a reciprocating spiral trajectory, that is, the radiation source 712 alternately performs a circular motion in a clockwise direction and a counterclockwise direction while moving in the first direction. In some embodiments, a cable may be connected between the C-shaped arm 710 and the radiation source 712. The length of the cable is limited, and the C-shaped arm 710 cannot rotate continuously. By scanning along the reciprocating spiral trajectory, the exposure range may be expanded and under the condition of ensuring sufficient data, problems such as cable entanglement caused by the continuous rotation of the C-shaped arm 710 may be avoided. Merely by way of example, the reciprocating spiral trajectory may be configured such that during the motion of the radiation source 712 in the first direction, the radiation source 712 first rotates clockwise by 270° or by other angles (such as 180°, 315°, 360°, etc.), and then rotates counterclockwise by 270° or by other angles (such as 180°, 315°, 360°, etc.). The process continues until the scan is completed. It should be noted that the clockwise rotation angle and the counterclockwise rotation angle may be the same or different. For example, the radiation source 712 may first rotate 27° clockwise, and then rotate more than 270° counterclockwise (e.g., 360°, 540°, etc.). In addition, during the motion of the radiation source 712 in the first direction, the radiation source 712 may further rotate counterclockwise first and then rotate clockwise.

In some embodiments, the controller may be configured to control the radiation source 712 to rotate in a circumferential direction by a certain angle (e.g., 180°, 270°, 360°, etc.) while moving in the first direction to scan. When the rotation ends, the radiation source 712 suspends the motion in the first direction, and rotates back in the circumferential direction. The data collection may not be performed during the back rotation. A back rotation angle may be the same as the previous rotation angle, or greater or less than the previous rotation angle. When the radiation source 712 completes the back rotation, the controller may control the radiation source 712 to continue to move in the first direction and the circumferential direction and perform data collection simultaneously, which may also avoid the entanglement of cables.

In some embodiments, the first direction is perpendicular to a circumferential plane formed when the radiation source 712 has the circular motion. The circumferential plane formed when the radiation source 712 has the circular motion may be understood as a circumferential plane formed when the radiation source 712 only has the circular motion without moving in the first direction. The fact that the first direction is perpendicular to the aforementioned circumferential plane may facilitate the scan, enlarge a scanning space, and make it easier for the subsequent image reconstruction.

In some embodiments, the first direction may form a first included angle β with a perpendicular line of the circumferential plane formed when the radiation source 712 has the circular motion, and the first included angle β is smaller than a preset threshold. The scanning trajectory of the radiation source 712 is shown in FIG. 9. In some embodiments, to avoid a motion interference among various devices (such as the interference between the C-shaped arm 710 and a scanning bed or the interference between the detector and the scanning bed, etc.), the set threshold of the first included angle β may be set as the maximum angle at which interference between the various devices may not occur during scanning. For example, the set threshold may be 15°, 30°, 45°, 50°, etc. By controlling the first direction to form the first included angle β with the perpendicular line of the circumferential plane formed when the radiation source 712 has the circular motion, the scanning system 700 based on the C-shaped arm 710 may adapt to scan lesions in different areas.

In some embodiments, when using the C-shaped arm 710 for a medical examination or treatment operation, it is usually used in conjunction with a scanning bed. The scanning bed may be used for an object to be examined or treated to lie flat or lie on it at a certain angle to facilitate the use of radiation for examination or treatment. At this time, the motion of the C-shaped arm 710 in the first direction may be understood as the motion of the C-shaped arm 710 along an extension direction of the scanning bed. That is, the first direction is the extension direction of the scanning bed. In some embodiments, due to certain errors in the device itself or in an adjustment process, the first direction may not be completely consistent with the extension direction of the scanning bed. In some embodiments, when the included angle between the first direction and the extension direction of the scanning bed is smaller than a certain threshold (e.g., 5°, 10°, etc.), the first direction may still be regarded as the extension direction of the scanning bed.

In some embodiments, the controller is configured to control the radiation source 712 to move in the first direction while performing a circular scanning motion within a scanning range. The scanning range covers a target scanning range. In some embodiments, when the radiation source 712 is located in a non-scanning range, the radiation source 712 may be controlled by the controller to quickly move to a position within the scanning range (e.g., the starting area of the scanning range), and then the radiation source 712 may be controlled to perform the circular scanning motion in the scanning range while moving in the first direction. The scanning range may be understood as a space where the radiation source 712 and the ray detector 711 perform data collection, and the target scanning range may be understood as a lesion area of the scanned object. By using the scanning range that covers the target scanning range, an effective data collection may be achieved for the lesion area of the scanned object. By controlling the radiation source 712 to move rapidly in the non-scanning range, the scanning efficiency may be effectively improved.

Referring again to FIG. 7, in some embodiments, the gantry may include a base 720 and a robotic arm assembly 730. The C-shaped arm 710 may be rotatably arranged at one end of the robotic arm assembly 730 away from the base 720. A position of the base 720 may remain fixed, and the motion of the C-shaped arm 710 in the first direction may be realized by the mechanical arm assembly 730. Preferably, the robotic arm assembly 730 includes a first robotic arm 731 and a second robotic arm 732. One end of the first robotic arm 731 is rotatably connected to the base 720, and the C-shaped arm 710 is rotatably arranged on an end of the second robotic arm 732 away from the first robotic arm 731. The controller controls the coordinated motion of the first robotic arm 731 and the second robotic arm 732 to realize the motion of the C-shaped arm 710 in the first direction. The C-shaped arm 710 is driven to move by the robotic arm assembly 730, and its motion is precise and stable, which is suitable for the medical device and has a high degree of automation. In some alternative embodiments, the robotic arm assembly 730 may further include a third robotic arm. The first robotic arm 731, the second robotic arm 732, and the third robotic arm are connected in sequence. The C-shaped arm 710 is arranged on one end of the third robotic arm. An expected motion mode may be achieved by the coordinated motion of the first robotic arm 731, the second robotic arm 732, and the third robotic arm. In addition, a driving manner of the robotic arm assembly 730 may include, but may not be limited to, one or more of a hydraulic driving, a pneumatic driving, a DC motor driving, an AC motor driving, a stepping motor driving, or an ultrasonic motor driving.

In some embodiments, the base 720 may be arranged on the ground or the ceiling. The arrangement of the base 720 may be designed according to actual needs. In the embodiment shown in FIG. 7, the base 720 is set on the ground. In addition, in some embodiments, the base 720 may further drive the robotic arm assembly 730 to rotate in a horizontal direction so as to further expand a working area of the scanning system.

In some embodiments, the scanning system described above may be a digital subtraction angiography (DSA) device. The DSA device is a kind of blood vessel examination device that combines a conventional angiography with a computer image processing technology, which can more clearly display the blood vessels and their lesions, and has a high application value. By cooperating with the scanning system with complete information collection and good reconstruction image quality in this embodiment, a detection cost may be greatly reduced, and difficulties in subsequent operations may be reduced to a certain extent. In some alternative embodiments, the aforementioned scanning system may further be applied to other scanning apparatuses, such as a peripheral interventional C-shaped arm, a C-shaped arm X-ray machine, etc.

The beneficial effects of the scanning system 700 based on the C-shaped arm 710 disclosed in the present disclosure may include but be not limited to: (1) through the circular motion and the motion in the first direction, the information collection during the scanning process may be more complete; (2) the complete information collection may improve the image reconstruction effect and greatly reduce the generation of artifacts; (3) when controlling the C-shaped arm 710 to scan, the problem of cable entanglement may not occur; (4) the scanning system 700 is applicable for lesions in different locations; (5) by using the robot arm assembly 730 for driving, the movement may be precise and stable, and the degree of automation may be high.

In some embodiments, the scanning apparatus may both scan the target object in a deflected state and drive the radiation source to move in the first direction while performing the circular scanning motion. Therefore, the scanning apparatus may not only obtain a larger reconstruction FOV, but also collect more information during the scanning process, thereby effectively improving the image reconstruction effect.

Figure 10:
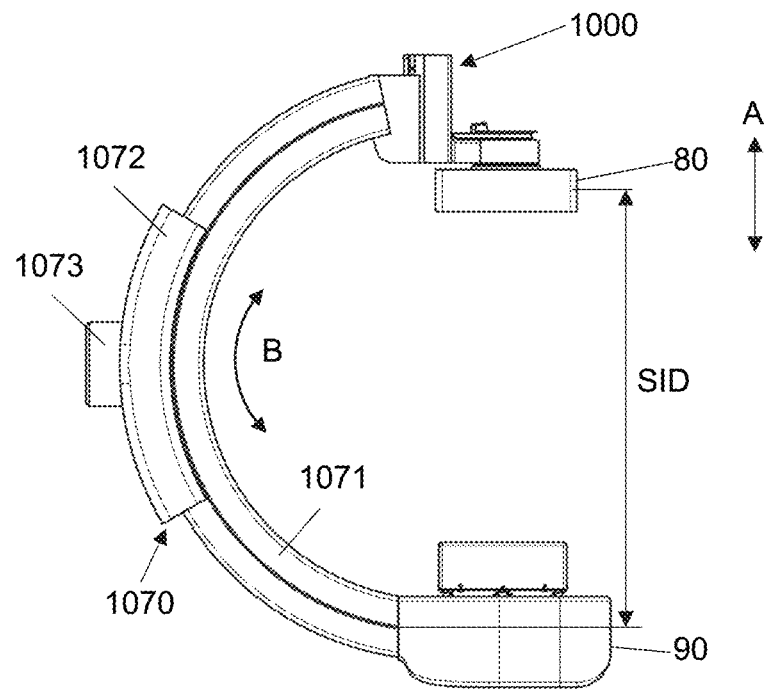
FIG. 10 is a schematic diagram illustrating a first state of a C-shaped main body part connected to a lift assembly according to some embodiments of the present disclosure.
Figure 11:
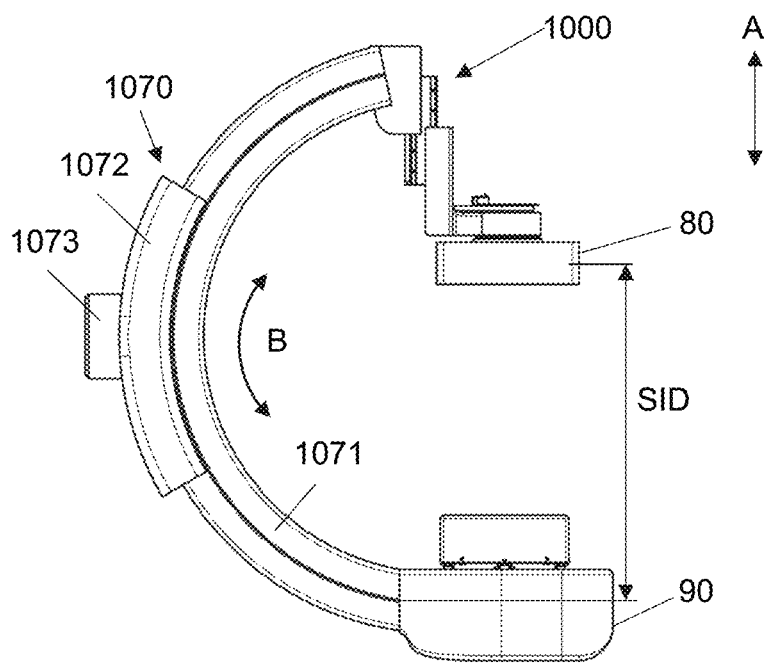
FIG. 11 is a schematic diagram illustrating a second state of a C-shaped main body part connected to a lift assembly according to some embodiments of the present disclosure.

One of the embodiments of the present disclosure provides a lift assembly and a C-shaped arm device (or a scanning apparatus) for an X-ray device. The X-ray device is a device configured to examine and diagnose various parts of the object. An operator may use its C-shaped arm device (or C-shaped main body part) to adjust the positions of the detector and the radiation source, and the scanning angle of the radiation source to satisfy different usage environments, thereby obtaining better X-ray images. Specifically, the DSA scanner may be taken as an example of the X-ray device. Referring to FIG. 10 and FIG. 11, the operator may need to adjust a distance between the radiation source 90 and the detector 80, namely the source to image receptor distance (SID), to adapt to different clinical shooting and imaging needs. Specifically, the SID may be a distance from a receiving surface of the detector 80 to a surface where a focal point of the radiation source 90 is located.

In some embodiments, the lift assembly for adjusting the SID includes a lift arm connected to the detector or the radiation source and a supporting shell for supporting the motion of the lift arm. The lift arm may move in an adjustment direction relative to the supporting shell to drive the motion of the detector or the radiation source, thereby realizing the distance adjustment of the SID. To satisfy a distance adjustment range of the SID, the supporting shell needs to provide enough moving path length for the lift arm, that is, the length of the supporting shell along the adjustment direction needs to be greater than or equal to the moving path length of the lift arm (that is, the maximum adjustment distance of the SID). That is to say, if the moving path length of the lift arm is L, the length of the supporting shell is at least L. The lift assembly in the aforementioned embodiment takes up a space dimension of the C-shaped arm device along the adjustment direction to the greatest extent. On the one hand, the overall dimension of the C-shaped arm device is increased, which is not compact in structure, but also brings inconvenience to the relevant spatial operation of the C-shaped arm. When the diameter of the C-shaped arm is the same, the supporting shell may extend outside for a distance from one end of the C-shaped main body. The extended supporting shell may hit the surrounding operators or other medical devices in the operating room. On the other hand, when the detector or the radiation source is adjusted to the maximum adjustment distance of the SID, that is, the detector and the radiation source are far away from each other, the detector and the radiation source may be located at the end of the supporting shell. There is at least one supporting shell with the length L in the adjustment direction of the detector and the radiation source, which affects the signal transmission between the detector and the radiation source to a certain extent.

Due to the above reasons, some embodiments of the present disclosure provide a lift assembly that can effectively solve the above problems. Please refer to FIGS. 10 and 11, FIGS. 10 and 11 are schematic diagrams of a first state and a second state of a C-shaped arm (a C-shaped main body part 1070) connected to a lift assembly according to some embodiments of the present disclosure. In FIG. 10, the C-shaped main body part 1070 is in a first state. In the first state, the SID may be the largest, and a lift assembly 1000 is in a contraction state. In FIG. 11, the C-shaped main body part 1070 is in a second state. In the second state, the SID is the shortest, and the lift assembly 1000 is in an extended state. In the present disclosure, a plurality of lift arms (for example, a target arm section, an intermediate arm section, etc.) may be linked by setting a linkage assembly, and the plurality of lift arms may be folded. As a result, under a condition that an adjustable SID range remains unchanged and when the distance between the detector 80 and the radiation source 90 is the largest, the dimension of the lift assembly 1000 may be smaller and the lift assembly 1000 may have a more compact structure, which is more convenient to meet the requirements of the C-shaped arm for the operating space, thereby making the C-shaped arm more suitable for the clinical operations. In some embodiments, as shown in FIGS. 10 and 11, the C-shaped main body part 1070 may further include a C-shaped arm body 1071 and a supporting gantry 1072. The C-shaped arm body 1071 is slidably connected to the supporting gantry 1072. As shown in FIG. 10 and FIG. 11, the C-shaped arm body 1071 is capable of arc-sliding in a direction of an arrow B relative to the supporting gantry 1072. In some embodiments, the supporting gantry 1072 may be provided with a main shaft 1073, and the supporting gantry 1072 may be rotatably connected to a gantry (e.g., a robotic arm) through the main shaft 1073.

Figure 12:
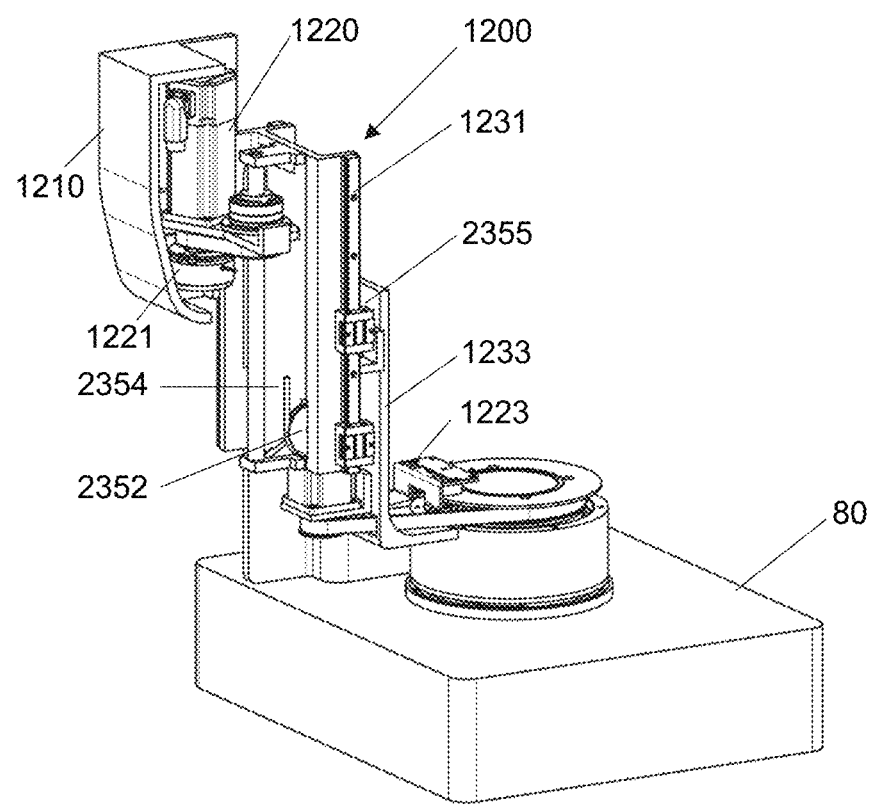
FIG. 12 is a first schematic diagram illustrating a connection between a lift assembly and a detector according to some embodiments of the present disclosure.
Figure 13:
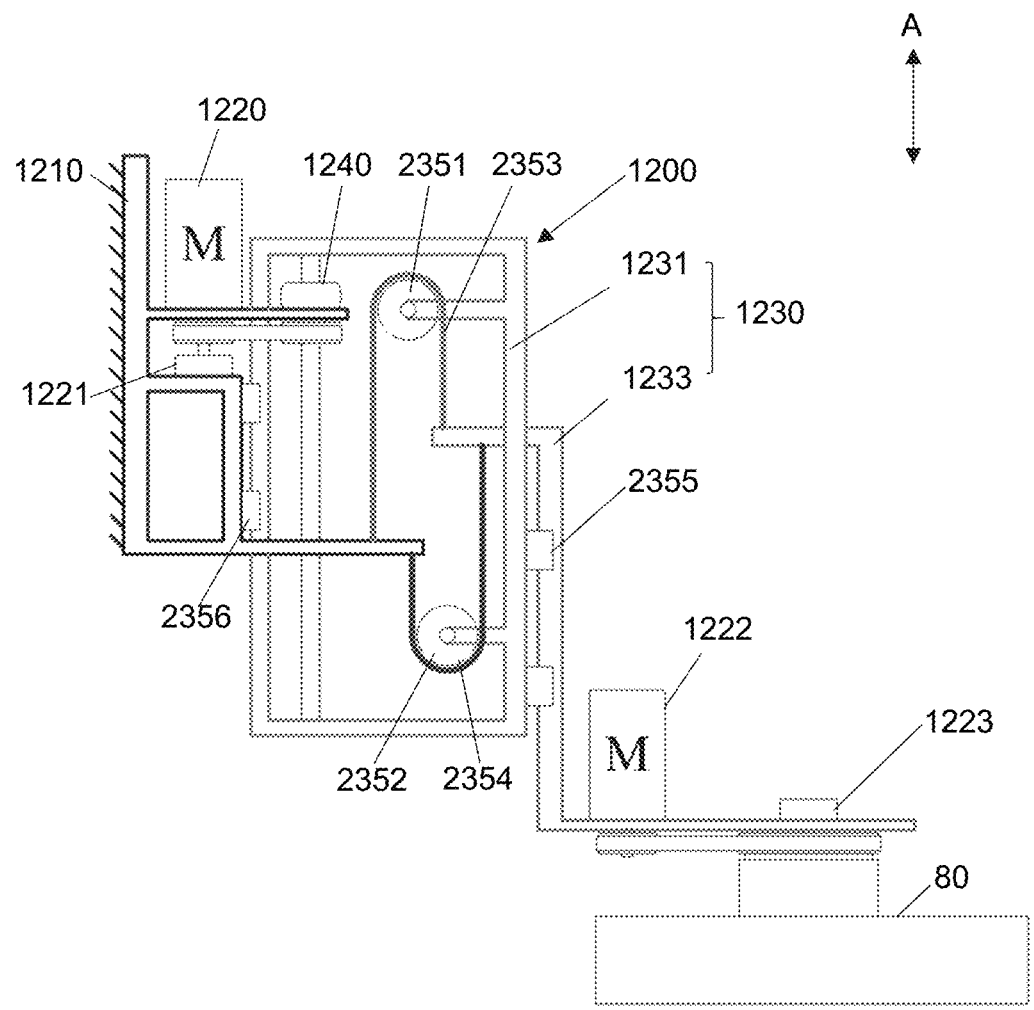
FIG. 13 is a second schematic diagram illustrating a connection between a lift assembly and a detector according to some embodiments of the present disclosure.

FIG. 12 is a first schematic diagram illustrating a connection between a lift assembly and a detector according to some embodiments of the present disclosure. FIG. 13 is a second schematic diagram illustrating a connection between a lift assembly and a detector according to some embodiments of the present disclosure. Referring to FIGS. 12 to 13, in some embodiments, a lift assembly 1200 includes: a shell 1210, a driving assembly 1220 accommodated in the shell 1210, and an arm adjustment assembly 1230. The arm adjustment assembly 1230 may move under the driving of the driving assembly 1220. The arm adjustment assembly 1230 includes an intermediate arm section 1231, a target arm section 1233, and a linkage assembly arranged between the intermediate arm section 1231 and the target arm section 1233. The intermediate arm section 1231 may move in the first direction under the driving of the driving assembly 1220. When the intermediate arm section 1231 moves in the first direction, the target arm section 1233 may be driven to move in the first direction by the linkage assembly, and projections of the intermediate arm section 1231 and the target arm section 1233 in the first direction at least partially overlap. The target arm section 1233 is connected to the detector 80 or the radiation source 90. In the embodiments shown in FIGS. 12 and 13, the target arm section 1233 may be connected to the detector 80. In other embodiments, the target arm section 1233 may further be connected to the radiation source 90. The shell 1210 is configured to accommodate and protect other assemblies. The first direction (denoted by arrow A in FIG. 13) may be understood as a direction perpendicular to a flat panel of the detector 80. In some embodiments, the first direction includes a first direction vertically downward and a first direction vertically upward. If the target arm section 1233 is driven to move vertically downward in the first direction, the distance between the detector 80 and the radiation source 90 may be reduced, and if the target arm section 1233 is driven to move vertically upward in the first direction, the distance between the detector 80 and the radiation source 90 may be increased.

In some embodiments, positions of the detector 80 and the radiation source 90 may be set at different positions according to clinical shooting and imaging requirements. For example, the detector 80 may be located above the radiation source 90 (as shown in FIG. 10 and FIG. 11), or the detector 80 may be located below the radiation source 90. The detector 80 above the radiation source 90 may be taken as an example to illustrate a process of adjusting the SID by the lift assembly 1200 in one or more embodiments of the present disclosure. If the SID needs to be reduced, the driving assembly 1220 may drive the intermediate arm section 1231 to move vertically downward in the first direction, and at the same time, the target arm section 1233 may move in the same direction with the intermediate arm section 1231 driven by the linkage assembly, and the detector 80 can be close to the radiation source 90. If the SID needs to be increased, the driving assembly 1220 may drive the intermediate arm section 1231 to move vertically upward in the first direction, and the target arm section 1233 may move in the same direction with the intermediate arm section 1231 driven by the linkage assembly, and the detector 80 can be far away from the radiation source 90.

In some embodiments, the projections of the intermediate arm section 1231 and the target arm section 1233 in the first direction at least partially may overlap. By the overlapping arrangement of the intermediate arm section 1231 and the target arm section 1233, the spatial dimension occupied in the first direction (i.e., the adjustment direction) may be reduced to a certain extent, thereby making the overall dimension of the lift assembly 1200 relatively small. The supporting shell may be provided with a small length space along the first direction, and the lift assembly 1200 makes the intermediate arm section 1231 have a short moving path length relative to the supporting shell through the linkage assembly, so that the target arm section 1233 can have a longer moving path length of along the first direction.

Specifically, as shown in FIGS. 10 and 11, when the SID is the smallest, the detector 80 and the radiation source 90 are closest to each other, and the intermediate arm section 1231 and the target arm section 1233 of the lift assembly 1200 are in the extended state (as shown in FIG. 11). According to the foregoing embodiments, since the intermediate arm section 1231 and the target arm section 1233 are linked through the linkage assembly, it is indicated that both the intermediate arm section 1231 and the target arm section 1233 have reached the maximum path length at this time. When the SID is the largest, the distance between the detector 80 and the radiation source 90 is the farthest, and the intermediate arm section 1231 and the target arm section 1233 of the lift assembly 1200 are in the contraction state (as shown in FIG. 10), it is indicated that the intermediate arm section 1231 and the target arm section are at an initial point (with a zero path length) at this time.

In some embodiments, when the lift assembly 1200 changes from the extended state to the contraction state, the projections of the intermediate arm section 1231 and the target arm section 1233 in the first direction at least partially overlap, indicating that in the process of contracting the lift assembly 1200, the dimension occupied by the target arm section 1233 and the intermediate arm section 1231 is reduced. In other words, the arm adjustment assembly is folded when the lift assembly 1200 is operated from the extended state to the contraction state. To sum up, under the condition that when the lift assembly 1200 provided by the present disclosure keeps the adjustable SID range at the maximum and unchanged, during the contracting process, the arm adjustment assembly may be folded, so that the lift assembly 1200 in the contraction state occupies a smaller overall size, which is more suitable for clinical operations.

Referring to FIGS. 12 and 13 again, in some embodiments, the linkage assembly includes a first support component 2351 and a second support component 2352 arranged on the intermediate arm section 1231, a first flexible traction component 2353 connected to the first support component 2351, and a second flexible traction component 2354 connected to the second support component 2352. One end of the first flexible traction component 2353 is connected to the shell 1210, and the other end of the first flexible traction component 2353 is connected to the target arm section 1233. One end of the second flexible traction component 2354 is connected to the shell 1210, and the other end of the second flexible traction component 2354 is connected to the target arm section 1233.

Referring to FIG. 13, the first support component 2351 and the second support component 2352 are respectively arranged on the intermediate arm section 1231 away from each other, and are respectively configured to support the first flexible traction component 2353 and the second flexible traction component 2354, so as to drive the target arm section 1233 to move through the two flexible traction components. As shown in FIG. 13, the first support component 2351 is arranged near an upper part of the intermediate arm section 1231, and the second support component 2352 is arranged near a lower part of the intermediate arm section 1231. In this embodiment, the first flexible traction component 2353 and the second flexible traction component 2354 both include two ends, and both the first flexible traction component 2353 and the second flexible traction component 2354 have one end fixed to the shell 1210. One end of the first flexible traction component 2353 is connected to the first support component 2351 and the other end of the first flexible traction component 2353 is bypassed from above the first supporting component 2351 and is fixedly connected to the target arm section 1233. One end of the second flexible traction component 2354 is connected to the second support component 2352 and the other end of the second flexible traction component 2354 is bypassed from below the second support component 2352 and is fixedly connected to the target arm section 1233. Since the first support component 2351 and the second support component 2352 may both move with the intermediate arm section 1233 during the moving process of the intermediate arm section 1233, a combination of the first support component 2351 and the first flexible traction component 2353 and a combination of the second support component 2352 and the second flexible traction component 2354 may be regarded as two movable pulley mechanisms, respectively. In this way, the linkage assembly connects the shell 1210 with the target arm section 1233 through the first flexible traction component 2353 and the second flexible traction component 2354, respectively.

The first flexible traction component 2353 and the second flexible traction component 2354 may respectively use the first support component 2351 and the second support component 2352 as fulcrums to form two movable pulley mechanisms, so as to realize the linkage between the target arm section 1233 and the intermediate arm section 1231.

It should be noted that the ends of the first flexible traction component 2353 and the second flexible traction component 2354 respectively fixed to the shell 1210 may be equivalent to the fixed ends in the movable pulley mechanisms. The ends of the first flexible traction component 2353 and the second flexible traction member 2354 respectively fixed to the target arm section 1233 may be equivalent to the moving ends of the movable pulley mechanisms. The moving path length of a moving end is twice the moving path length of a pulley of each movable pulley mechanism (for example, the first support component 2351 or the second support component 2352).

The specific process of the linkage of the lift assembly 1200 of the present disclosure is as follows: when reducing the SID, for example, when the detector 80 in FIG. 13 needs to be controlled to move vertically downward in the first direction, the intermediate arm section 1231 needs to be controlled to move vertically downward in the first direction, and the first support component 2351 and the second support component 2352 fixed to the intermediate arm section 1231 may also move vertically downward in the first direction. The moving path lengths of the first support component 2351 and the second support component 2352 are the same as the moving path length of the intermediate arm section 1231. Since one end of the first flexible traction component 2353 and one end of the second flexible traction component 2354 are both fixed to the shell 1210 and the shell 1210 is fixed, the moving end of the first flexible traction component 2353 and the moving end of the second flexible traction component 2354 may move vertically downward in the first direction, and the target arm section 1233 may move accordingly. Moreover, the moving path length of the target arm section 1233 is the same as the moving path length of the moving end of one of the flexible traction components, and is twice the moving path length of the intermediate arm section 1231. Similarly, when increasing the SID, for example, when the detector 80 in FIG. 13 needs to be controlled to move vertically upward in the first direction, the intermediate arm section 1231 needs to be controlled to move vertically upward in the first direction, and the first support component 2351 and the second support component 2352 fixed to the intermediate arm section 1231 may also move vertically upward along the first direction. The moving path lengths of the first support component 2351 and the second support component 2352 are the same with the moving path length of the intermediate arm section 1231. The moving end of the first flexible traction component 2353 may move vertically upward in the first direction due to a pulling force, thus driving the target arm section 1233 to move vertically upward in the first direction. At the same time, the moving end of the second flexible traction component 2354 may also move vertically upward in the first direction. The moving path length of the target arm section 1233 is the same as the moving path length of the moving end of one of the flexible traction components, and is twice the moving path length of the intermediate arm section 1231.

In some embodiments, the linkage assembly including the first support component 2351 and the second support component 2352 may ensure that both the target arm section 1233 and the intermediate arm section 1231 may be driven by the driving assembly 1220 and achieve a linkage effect when the lift assembly 1200 is at any angle (e.g., tilted 30°, 45°, 60°, etc., relative to the lift assembly 1200 in FIG. 12).

In some embodiments, the first support component 2351 and the second support component 2352 may be arranged at opposite ends of the intermediate arm section 1231. For example, as shown in FIG. 13, the first support component 2351 is arranged at the upper end of the intermediate arm section 1231, and the second support component 2352 is arranged at the lower end of the intermediate arm section 1231. The distance between the first support component 2351 and the second support component 2352 may affect the adjustable SID range of the lift assembly 1200. For example, the shorter the distance between the first support component 2351 and the second support component 2352 is, the smaller the adjustable SID range is, and the longer the distance between the first support component 2351 and the second support component 2352 is, the greater the adjustable SID range is.

In some embodiments, the first support component or the second support component includes a pulley or a sprocket. The first flexible traction component or the second flexible traction component includes a rope (such as a steel wire rope) connected to the pulley or a chain connected to the sprocket.

In some embodiments, the pulley and the intermediate arm section 1231 may be relatively fixed, i.e., the pulley cannot move. In some other embodiments, the pulley and the intermediate arm section 1231 may move relative to each other, that is, the pulley can move, so as to reduce the wear between the rope and the pulley.

Similar to the pulley and the rope, after the sprocket and the chain are engaged, one end of the chain is fixed to the shell 1210, and the other end of the chain is fixed to the target arm section 1233, which can also form a moving pulley mechanism, and the cooperation between the sprocket and the chain is more stable.

With regard to the flexible traction components and the corresponding support components, the present disclosure may also include other embodiments that can achieve similar functions, which may not be repeated here. In addition, in other embodiments not disclosed in the present disclosure, at least one other arm section may be added on the basis of the intermediate arm section 1231 and the target arm section 1233. Under a condition that the moving path length of the target arm section 1233 remains unchanged, the dimension of the supporting shell in the adjustment direction may be further reduced. Specifically, for example, a third arm section may be provided between the intermediate arm section 1231 and the target arm section 1233. A linkage assembly similar to that described above is provided between the intermediate arm section 1231 and the third arm section, and a linkage assembly similar to that described above is provided between the third arm section and the target arm section 1233. The driving assembly 1220 drives the intermediate arm section 1231 to move, the intermediate arm section 1231 drives the third arm section to move, and the third arm section drives the target arm section 1233 to move. When a moving distance of the intermediate arm section 1231 in the first direction is s, a moving distance of the third arm section is 2 s, and a moving distance of the target arm section is 4 s.

Please refer to FIG. 12 and FIG. 13 again, in some embodiments, the linkage assembly further includes a first sliding block 2355 and a first guiding rail matching the first sliding block 2355. The first sliding block 2355 is arranged on one of the intermediate arm section 1231 and the target arm section 1233, and the first guiding rail is arranged on the other one of the intermediate arm section 1231 and the target arm section 1233. In this embodiment, the first sliding block 2355 and the first guiding rail may form a guiding support for the target arm section 1233 to ensure that when the target arm section 1233 moves with the intermediate arm section 1231, the target arm section 1233 may not deviate from the moving direction, thereby ensuring the imaging quality of the X-ray device.

In some embodiments, the first sliding block 2355 and the first guiding rail may be arranged on one and the other one of the target arm section 1233 and the intermediate arm section 1231, respectively. For example, the first sliding block 2355 may be arranged on the target arm section 1233, and the first guiding rail may be arranged on the intermediate arm section 1231. Similarly, the first sliding block 2355 may be arranged on the intermediate arm section 1231, and the first guiding rail may be arranged on the target arm section 1233.

In some alternative embodiments, other assemblies may be used to form the guiding support of the target arm section 1233, which includes but is not limited to a pulley matched with a sliding rail, a ball matched with a sliding rail, a gear matched with a sliding rail, etc.

In other alternative embodiments, the guiding support (e.g., the sliding block and the guiding rail, etc.) may not be provided so as to reduce a weight of the lift assembly 200 and simplify the structure.

As shown in FIG. 13, in some embodiments, the lift assembly 1200 further includes a second sliding block 2356 arranged between the shell 1210 and the intermediate arm section 1231 and a second guiding rail matched with the second sliding block 2356. The second sliding block 2356 is arranged on one of the shell 1210 and the intermediate arm section 1231, and the second guiding rail is arranged on the other one of the shell 1210 and the intermediate arm section 1231. In this embodiment, the first sliding block 2355 and the first guiding rail may form a guiding support for the target arm section 1233 to ensure that when the target arm section 1233 moves with the intermediate arm section 1231, the target arm section 1233 may not deviate from the moving direction (for example, vertically upward and downward in the first direction), thereby ensuring the imaging quality of the X-ray device.

In some embodiments, the second sliding block 2356 and the second guiding rail may be arranged on one and the other one of the shell 1210 and the intermediate arm section 1231, respectively. For example, the second sliding block 2356 may be arranged on the shell 1210, and the second guiding rail may be arranged on the intermediate arm section 1231. Similarly, the second sliding block 2356 may be arranged on the intermediate arm section 1231, and the second guiding rail may be arranged on the shell 1210. The second sliding block 2356 with the second guiding rail are the same as or similar to the first sliding block 2355 with the first guiding rail, and the related descriptions may be found in other embodiments of the present disclosure, which may not be repeated here.

In some embodiments, the driving assembly 1220 is a device configured to drive the target arm section 1233 to move. The driving assembly 1220 may include a linear output assembly. In some embodiments, the linear output assembly may include but be not limited to, a linear motor, etc. In some embodiments, the driving assembly 1220 may include a rotary output assembly, e.g., a rotary output motor (shown as 1220 in FIG. 13). Compared with the linear output assembly, the rotary output assembly does not occupy the dimension of the lift assembly 1200 in the first direction, which is more convenient for the C-shaped arm to adapt to the clinical operations.

Please refer to FIG. 13 again, in some embodiments, the lift assembly 1200 may further include a transmission assembly arranged between the driving assembly 1220 and the intermediate arm section 1231 configured for a transmission between the driving assembly and the intermediate arm section. In some specific embodiments, the transmission assembly may include a motion conversion mechanism 1240 that converts a rotary motion to a linear motion. In this embodiment, the motion conversion mechanism 1240 may be used in conjunction with the rotary output assembly. The motion conversion mechanism 1240 may be configured to convert the rotary motion output by the driving assembly 1220 (e.g., the motor shown as 1220 in FIG. 13) into a linear motion of the intermediate arm section 1231, which may further reduce the overall dimension of the lift assembly 1200.

Further, in some specific embodiments, the motion conversion mechanism 1240 may further include but be not limited to, a screw nut structure, a rack and pinion structure, a crank slider structure, a cam structure, a trapezoidal thread structure, etc. The specific structure of the motion conversion mechanism 1240 may be determined based on the actual situation.

Taking the screw nut structure as an example, the screw nut structure includes a nut (not shown in the figure) that is rotatable relative to the shell 1210, and a screw (not shown in the figure) located at a fixed location relative to the intermediate arm section 1231. The nut is threadedly connected to the screw, and the nut is driven by the driving assembly 1220.

Since the rotary output assembly of the driving assembly 1220 is relatively fixed to the nut, when the driving assembly 1220 is running, the nut may be driven to rotate, and the nut may drive the screw to rotate and move in the first direction to adjust the SID. The screw nut structure using such a transmission manner may eliminate an axial motion generated by the screw and obtain a higher transmission accuracy, which is suitable for a scenario in which the SID is adjusted in a small range. In some embodiments, the driving assembly 1220 may further include a timing belt (not shown in the figure). The timing belt may transmit a kinetic energy of the motor to the screw nut structure, and drive the nut to rotate to drive the screw to ascend and descend.

In some alternative embodiments, the driving assembly 1220 may directly drive the screw to move, and correspondingly the nut is relatively fixed to the intermediate arm section 1231. When the driving assembly 1220 is running, the screw may be driven to rotate, and the screw may drive the nut to move in the first direction, which can also achieve the purpose of adjusting the SID. The screw nut structure using such a transmission manner may have a screw with good rigidity and is suitable for a scenario in which the SID is adjusted in a wide range.

In some embodiments, an operator may control the lift assembly 1200 to adjust the SID through an external controller (not shown) connected with the driving assembly 1220. In some embodiments, the system may automatically adjust the SID according to a protocol, and the operator may also adjust the SID roughly or precisely on an interactive interface. For example, the operator may input a value of the SID on the external controller or directly click a button to increase or reduce the value of the SID to control the lift assembly 1200 to adjust the detector 80 and the radiation source 90 to the positions corresponding to the SID value. In some embodiments, the SID may also be adjusted more roughly. For example, the operator may control the operation of the lift assembly 1200 to reduce or increase the SID through a switch. When the lift assembly 1200 adjusts the detector 80 and the radiation source 90 to proper positions, the operator may turn off the switch and the lift assembly 1200 may stop operating. In some embodiments, the external controller may have the above two adjustment functions at the same time, that is, the operator may perform both rough adjustment and precise adjustment. For example, when the adjustable SID range is large, the operator may first perform the rough adjustment, and perform the precise adjustment after the detector 80 and the radiation source 90 reaches approximate positions. Compared to using a single function to adjust, the aforementioned manner may save time and ensure the adjustment accuracy.

Please refer to FIG. 13 again, in some embodiments, the driving assembly 1220 may further include a first brake 1221 configured to prevent the target arm section 1233 from falling down due to braking or abnormal driving of the intermediate arm section 1231.

In some embodiments, the target arm section 1233 and the detector 80 or the radiation source 90 may be relatively fixedly connected, for example, a central radiation beam of the radiation source 90 is perpendicular to the flat panel of the detector 80. In other embodiments, the detector 80 or the radiation source 90 and the target arm section 1233 may rotate relative to each other. For example, the detector 80 may rotate relative to the target arm section 1233, or the radiation source 90 may rotate relative to the target arm section 1233, or both the detector 80 and the radiation source 90 may rotate relative to the target arm section 1233, which is more convenient to meet different imaging requirements and obtain images with higher quality.

In some embodiments, the lift assembly 1200 may further include a second driving assembly (e.g., shown as 1222 in FIG. 13) arranged on the target arm section 1233. The second driving assembly 1222 may drive the detector 80 or the radiation source 90 to rotate through a transmission assembly (e.g., a timing belt), so that the object to be examined and the detector 80 may receive sufficient X-ray exposure.

In some embodiments, the second driving assembly 1222 may further include a second brake 1223 for protecting the detector 80 or the radiation source 90 to prevent abnormal rotation drive.

In some embodiments, the first support component 2351, the second support component 2352, the first flexible traction component 2353, and the second flexible traction component 2354 may form a linkage device, so that the shell 1210, the intermediate arm section 1231, and the target arm section 1233 may be linked with each other. In some embodiments, when the driving assembly 1220 (such as a motor) rotates, the intermediate arm section 1231 may be driven up and down through the transmission assembly. While the intermediate arm section 1231 is moving up and down, due to the action of the linkage device (such as the first support component 2351, the second support component 2352, the first flexible traction component 2353, and the second flexible traction component 2354), the target arm section 1233 may move accordingly, so as to realize the lifting movement of the detector 80 (or the radiation source 90). In some embodiments, the shell 1210, the intermediate arm section 1231, and the target arm section 1233 may be slidably supported by a linear guiding rail and a sliding block (e.g., the first sliding block 2355 and the second sliding block 2356). The shell 1210, the intermediate arm section 1231, and the target arm section 1233 may slide with respect to each other to stretch and expand, or overlap with each other to retract to achieve the SID adjustment, that is, the rise and fall of the detector 80 (or the radiation source 90).

Figure 14:
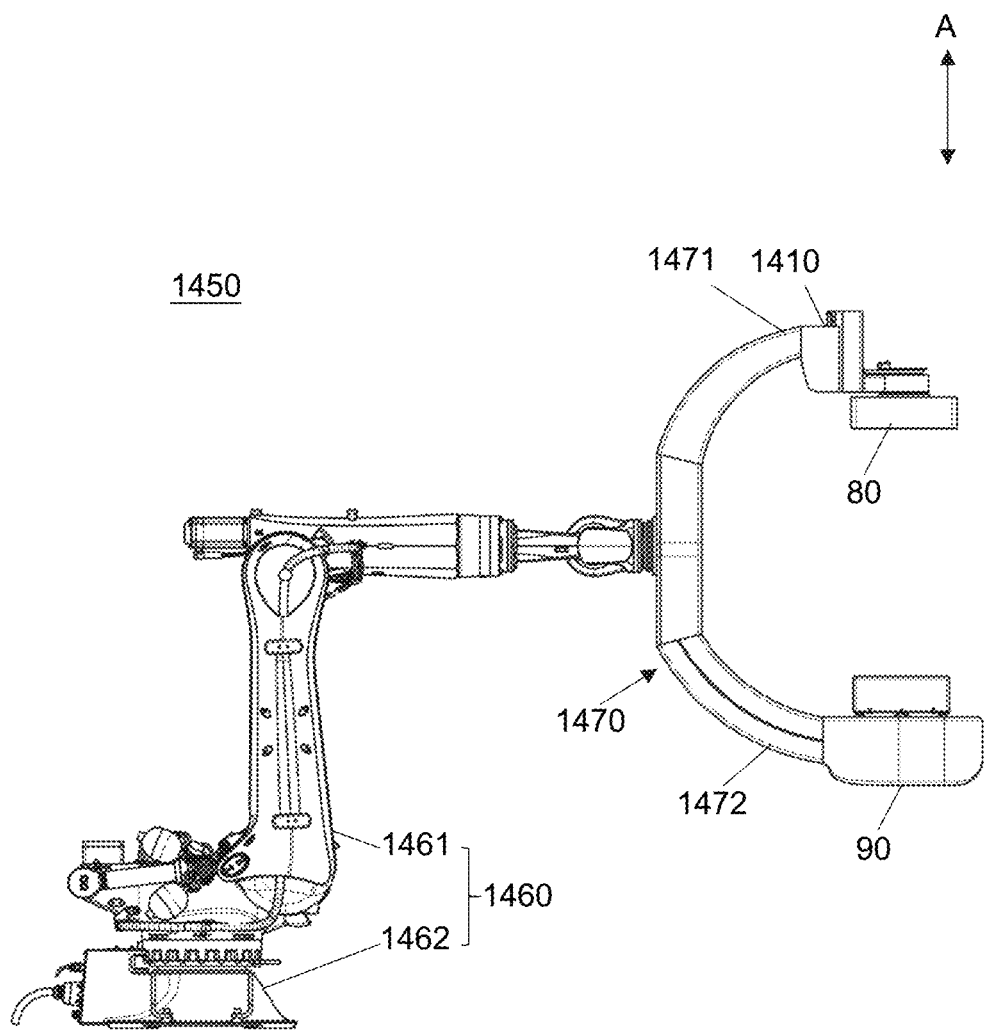
FIG. 14 is a schematic diagram illustrating a first state of a C-shaped arm device according to some embodiments of the present disclosure.
Figure 15:
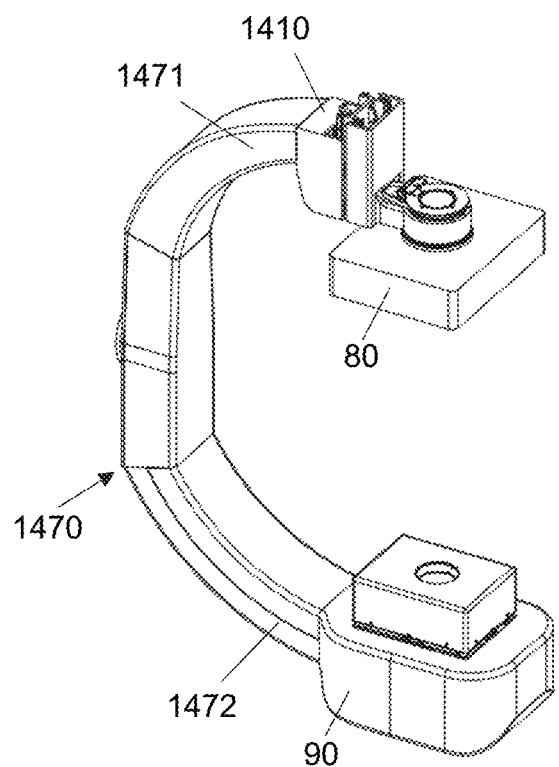
FIG. 15 is a schematic diagram illustrating a three-dimensional structure of a first state of a C-shaped arm device according to some embodiments of the present disclosure.
Figure 16:
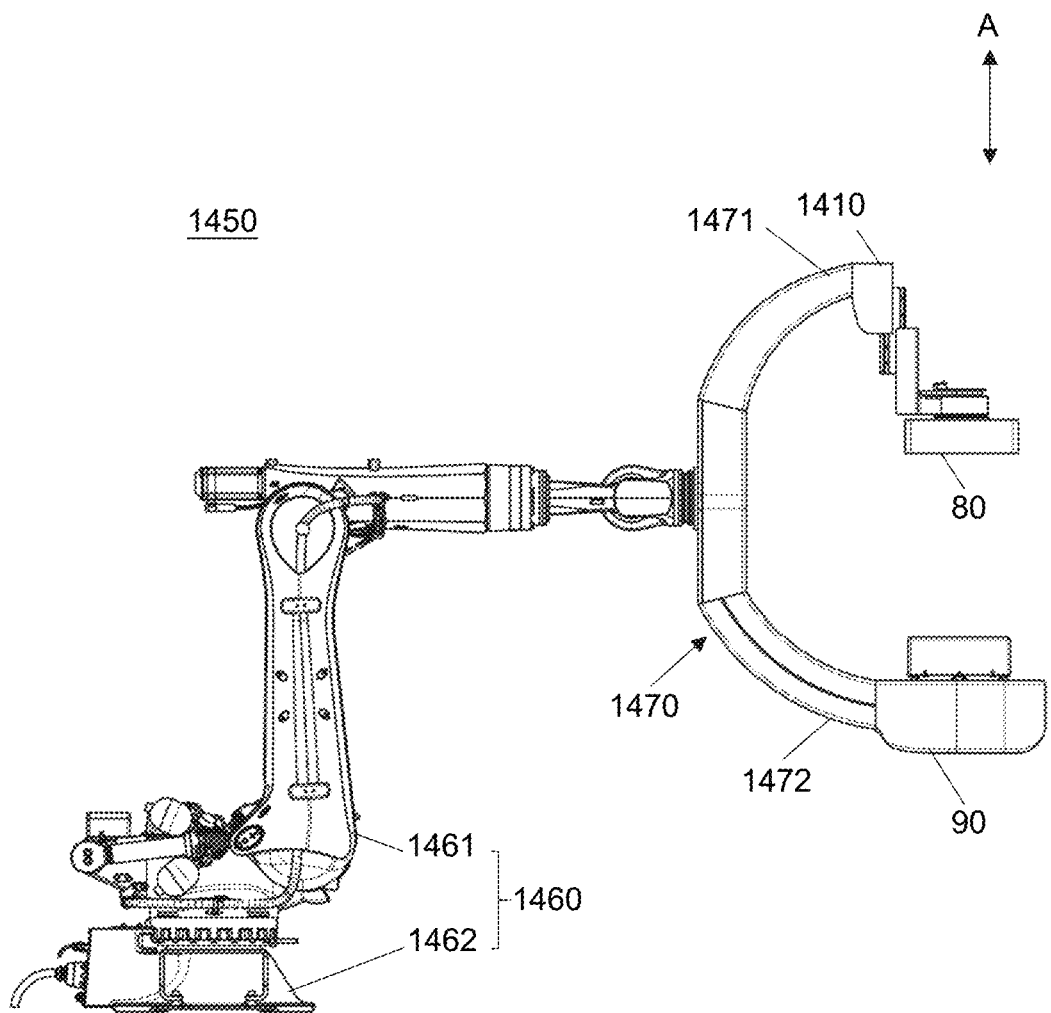
FIG. 16 is a schematic diagram illustrating a second state of a C-shaped arm device according to some embodiments of the present disclosure.
Figure 17:
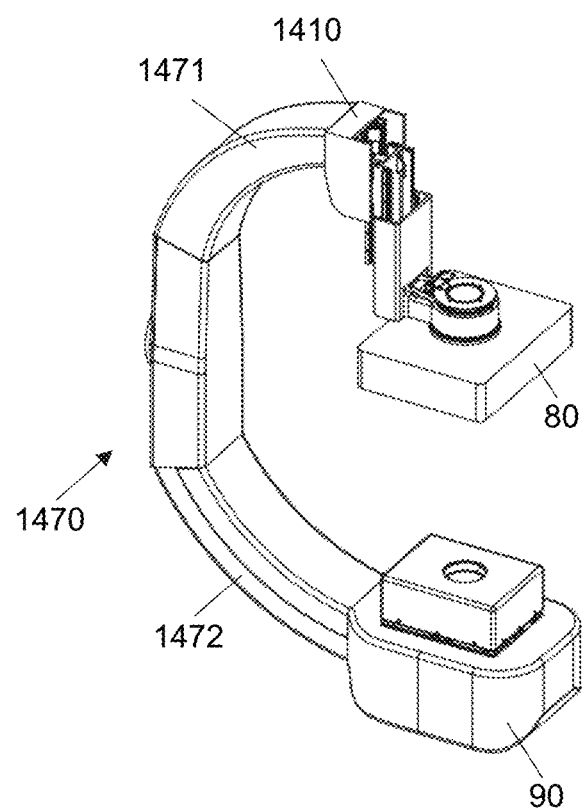
FIG. 17 is a schematic diagram illustrating a three-dimensional structure of a second state of a C-shaped arm device according to some embodiments of the present disclosure.

Other embodiments of the present disclosure further provide a C-shaped arm device for an X-ray machine. FIG. 14 is a schematic diagram illustrating a first state of a C-shaped arm device according to some embodiments of the present disclosure. FIG. 15 is a schematic diagram illustrating a three-dimensional structure of a first state of a C-shaped arm device according to some embodiments of the present disclosure. FIG. 16 is a schematic diagram illustrating a second state of a C-shaped arm device according to some embodiments of the present disclosure. FIG. 17 is a schematic diagram illustrating a three-dimensional structure of a second state of a C-shaped arm device according to some embodiments of the present disclosure. As shown in FIGS. 14-17, in some embodiments, the C-shaped arm device 1450 may include a supporting main body part 1460, a C-shaped main body part 1470 connected to the supporting main body part 1460, a detector 80 connected to a first end 1471 of the C-shaped main body part 1470, and a radiation source 90 connected to a second end 1472 of the C-shaped main body part 1470. At least one of the detector 80 or the radiation source 90 may be connected to the C-shaped main body part 1470 through the lift assembly 1200 described above. The lift assembly 1200 at least includes a driving assembly 1220, a first movable part, and a second movable part. On a source image distance adjustment path defined by the detector 80 and the radiation source 90 and under the driving of the driving assembly 1220, the first movable part relative to the C-shaped main body part 1470 may move in a same direction as a direction along the source image distance adjustment path, and the second movable part relative to the first movable part may also move in the same direction as the direction along the source image distance adjustment path to adjust a source image distance.

In some embodiments, the first movable part may be equivalent to the intermediate arm section 1231 in the foregoing embodiments, and the second movable part may be equivalent to the target arm section 1233 in the foregoing embodiments. When the first movable part moves relative to the C-shaped main body part 1470, the second movable part also moves relative to the first movable part. In some embodiments, a moving distance of the second movable part may be greater than a moving distance of the first movable part, e.g., the moving distance of the second movable part is twice the moving distance of the first movable part.

In some embodiments, the lift assembly 1200 may further include a third movable part. The third movable part may be driven and move in a same direction as the direction along the source image distance adjustment path to adjust the source image distance. In some embodiments, the third movable part may be arranged between the first movable part and the second movable part. If the lift assembly 1200 includes the third movable part, the second movable part may be equivalent to the target arm section 1233 in the foregoing embodiments, and the third movable part may be equivalent to the third arm section in the foregoing embodiments. In some embodiments, the moving distance of the first movable part may be less than a moving distance of the third movable part, and the moving distance of the third movable part may be less than the moving distance of the second movable part, e.g., a ratio of the moving distances of the first movable part, the third movable part, and the second active part may be 1:2:4.

In some embodiments, the source image distance may be equivalent to the SID in the foregoing embodiments, that is, a distance from a receiving plane of the detector 80 to a plane where the focal point of the radiation source 90 is located. The source image distance adjustment path may be equivalent to the first direction in the foregoing embodiment, which is vertically upward or vertically downward.

In some embodiments, the supporting main body part 1460 (or be referred to as a gantry) may have a supporting function in the C-shaped arm assembly. In some embodiments, as shown in FIGS. 14-17, the supporting main body part 1460 may include a robotic arm device 1461 and a base 1462. The robotic arm device 1461 may be connected to the C-shaped main body part 1470, and the robotic arm device 1461 may adjust the position of the whole C-shaped arm device through the robotic arm device 1461. The base 1462 may be connected to the robotic arm device 1461 and be configured to fix and support the robotic arm device 1461. In some embodiments, the robotic arm device 1461 may rotate relative to the base 1462. In some embodiments, the robotic arm device 1461 may be a multi-degree-of-freedom flexible robotic arm or a rigid robotic arm. The flexible robotic arm may be bent by using a lightweight elastic rod as its main structure, such as an octopus arm, an elephant trunk and other biological organ bionic robotic arms. The rigid robotic arm may be composed of rigid links with discrete joints, such as the robotic arm of an industrial robot. In some embodiments, the robotic arm device 1461 may include a data transmission system (not shown in the figure) configured to transmit image data obtained by the detector 80 to a computer system (not shown in the figure) of the X-ray device for image processing. In some embodiments, the robotic arm device may be applied to medium and small size C-shaped arm X-ray machines to perform a partial angiography operation, a partial photography operation, a complex interventional operation, etc.

Figure 18:
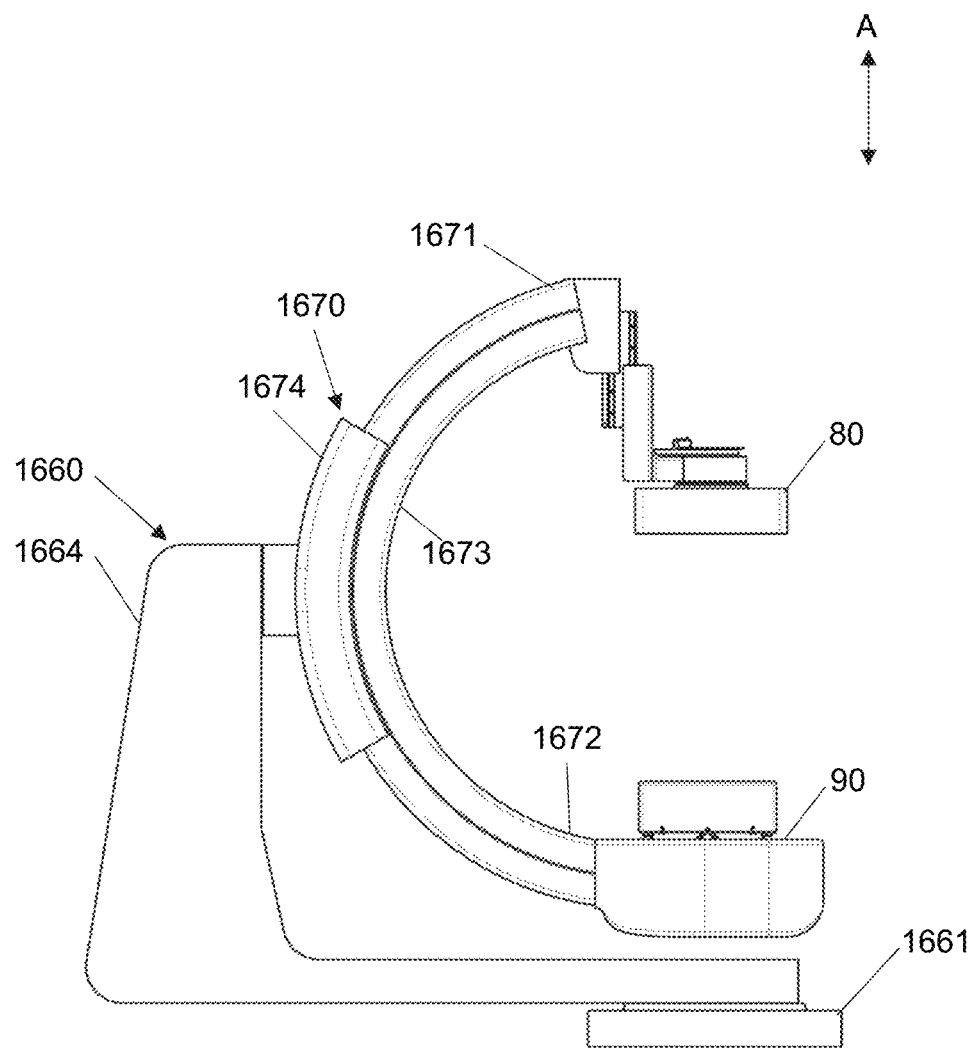
FIG. 18 is a first schematic diagram illustrating a connection between other supporting main body parts and a C-shaped main body part according to some embodiments of the present disclosure.
Figure 19:
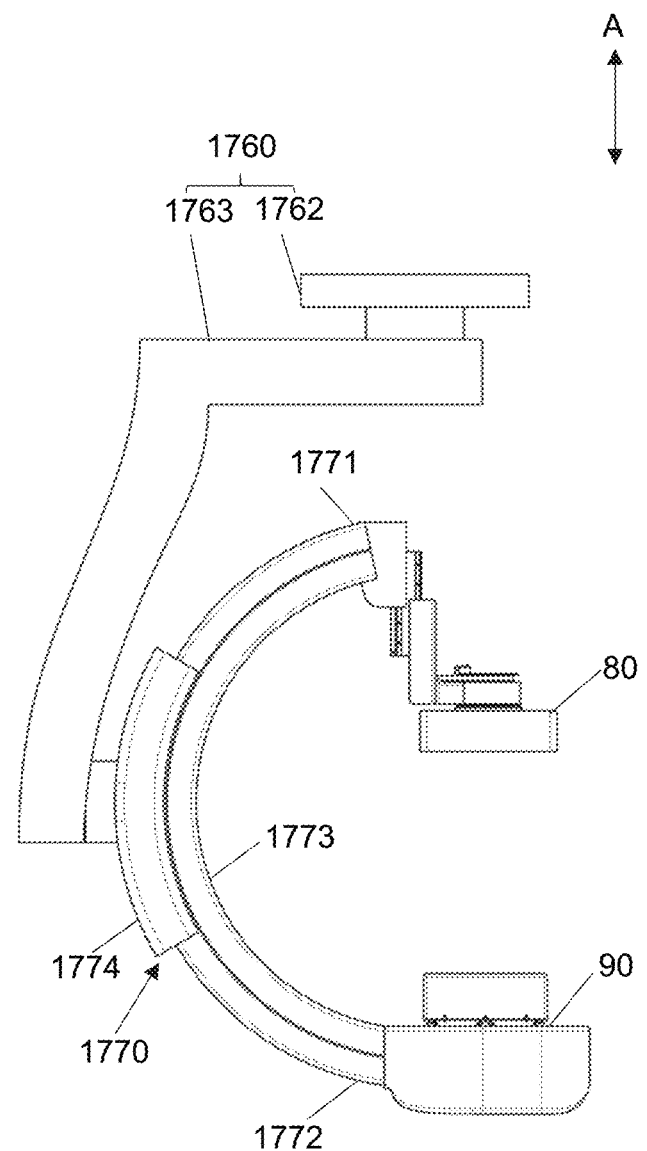
FIG. 19 is a second schematic diagram illustrating a connection between other supporting main body parts and a C-shaped main body part according to some embodiments of the present disclosure.

FIG. 18 is a first schematic diagram illustrating a connection between other supporting main body parts and a C-shaped main body part according to some embodiments of the present disclosure. FIG. 19 is a second schematic diagram illustrating a connection between other supporting main body parts and a C-shaped main body part according to some embodiments of the present disclosure. Referring to FIG. 18, in some alternative embodiments, a supporting main body part 1660 may further include a base 1661 and a gantry 1664. Referring to FIG. 19, in some other alternative embodiments, a supporting main body part 1760 may further include a base 1762 and a suspension device 1763. The base 1762 may be fixed on the ceiling, so that a C-shaped main body part 1770 may be suspended in the air. In some embodiments, the suspension device 1763 may be a conventional suspension block. In some embodiments, the suspension device 1763 and the aforementioned gantry may be applied to a large-sized C-shaped arm X-ray machine to realize the examination of an abdominal vasculature, an extremity vasculature, etc.

In some embodiments, the operator may employ different types of C-shaped main body parts according to the requirements of the clinical operation. In some embodiments, as shown in FIGS. 14 and 16, the C-shaped main body part 1470 may be the C-shaped arm. In some alternative embodiments, referring to FIG. 18 or FIG. 19, the C-shaped main body part 1670 (or 1770) may include a first arc body 1673 (or 1773) and a second arc body 1674 (or 1774). The first arc body 1673 (or 1773) includes a first end 1671 (or 1771) and a second end 1672 (or 1772) that are respectively connected to the detector 80 and the radiation source 90, and the second arc body 1674 (or 1774) is connected to the supporting main body part 1660 (or 1760). In some embodiments, the first arc body 1673 (or 1773) and the second arc body 1674 (or 1774) may rotate relative to each other. In this way, a special placement angle between a connection line between the detector 80 and the radiation source 90 and the object observed may be present, so that the operator can observe images at some angles in a targeted manner. In some embodiments, the first arc body 1673 (or 1773) may be provided with a third sliding block (not shown in the figure), and the second arc body 1674 (or 1774) may be provided with a third guiding rail (not shown in the figure) connecting the third sliding block, thereby realizing the rotation of the first arc body 1673 (or 1773) in the second arc body 1674 (or 1774).

Please refer to FIGS. 14-17 again, in some embodiments, the lift assembly 1200 and the two ends of the C-shaped main body part 1470 may be movably connected or fixedly connected. In some specific embodiments, the movable connection may include a relative rotation connection between the shell 1410 of the lift assembly 1200 and the two ends of the C-shaped main body 1470. The relative rotation connection may make the lift assembly 1200 rotate relative to both ends of the C-shaped main body 1470, so that the connection line between the detector 80 and the radiation source 90 forms an angle with the first direction, thereby realizing the multi-directional X-ray imaging. In some embodiments, the movable connection may include a relative sliding connection between the shell 1410 of the lift assembly 1200 and the two ends of the C-shaped main body part 1470. The relative sliding connection may further adjust the position of the lift assembly 1200 in the first direction, thereby adjusting the distance between the detector 80 and the radiation source 90. In some embodiments, the fixed connection may indicate that the lift assembly 1200 is fixed connected to both ends of the C-shaped main body 1470 by means of welding or fastening.

In some embodiments, the detector 80 may be connected to the first end 1471 of the C-shaped main body part 1470 through the shell 1410 of the lift assembly 1200, and the radiation source 90 may be connected to the second end 1472 of the C-shaped main body part 1470 using a relatively fixed or rotatable connection manner. When adjusting the distance between the detector 80 and the radiation source 90, the detector 80 may move vertically upward or vertically downward in the first direction through the lift assembly 1200, while the radiation source 90 remains unchanged in the first direction relative to the detector 80. As shown in FIG. 16, when the detector 80 moves vertically downward along the first direction to a position corresponding to the maximum displacement, the lift assembly 1200 may be in an extended state, and the distance between the detector 80 and the radiation source 90 may be the smallest. On the contrary, as shown in FIG. 14, when the detector 80 moves vertically upward along the first direction to a position corresponding to the maximum displacement, the lift assembly 1200 may be in the contraction state, and the distance between the detector 80 and the radiation source 90 may be the greatest.

In some alternative embodiments, the radiation source 90 may be connected to the second end 1472 of the C-shaped main body part 1470 through the shell 1410 of the lift assembly 1200, and the detector 80 may be connected to the first end 1471 of the C-shaped main body part 1470 using a relatively fixed or rotatable connection manner. When adjusting the distance between the detector 80 and the radiation source 90, the radiation source 90 may move vertically upward or vertically downward in the first direction through the lift assembly 1200, while the detector 80 remains unchanged in the first direction relative to the radiation source 90. When the radiation source 90 moves vertically downward along the first direction to a position corresponding to the maximum displacement, the lift assembly 1200 may be in the contraction state, and the distance between the detector 80 and the radiation source 90 may also be the greatest. On the contrary, when the radiation source 90 moves vertically upward along the first direction to a position corresponding to the maximum displacement, the lift assembly 1200 may be in the extended state, and the distance between the detector 80 and the radiation source 90 may also be the smallest.

In other alternative embodiments, the detector 80 and the radiation source 90 may be respectively connected to the first end 1471 and the second end 1472 of the C-shaped main body part 1470 through the shell 1410 of the lift assembly 1200. In this way, the detector 80 and the radiation source 90 may move in the first direction relative to the C-shaped main body part 1470. When adjusting the distance between the detector 80 and the radiation source 90, the detector 80 and the radiation source 90 may move in the first direction. When the two lifting assemblies 1200 respectively connected to the detector 80 and the radiation source 90 are both in the contraction state, the detector 80 and the radiation source 90 may both be in their corresponding initial positions, the path length may be zero, and the distance between the detector 80 and the radiation source 90 may be the largest. When the two lifting assemblies 1200 respectively connected to the detector 80 and the radiation source 90 are both in the extended state, the detector 80 moves vertically downward along the first direction to a position corresponding to the maximum displacement, and the radiation source 90 moves vertically upward along the first direction to a position corresponding to the maximum displacement, the distance between the detector 80 and the radiation source 90 may be the smallest. In this embodiment, the adjustable SID ranges of the two lifting assemblies 1200 may be the same or different. In some embodiments, the distance between the detector 80 and the radiation source 90 may be adjusted according to different application scenarios. For example, when the SID is clearly defined, only one of the detector 80 and the radiation source 90 may be adjusted to move for a certain distance in the first direction, or the detector 80 and the radiation source 90 may both be adjusted to move for a certain distance in the first direction.

The beneficial effects of the lift assembly and the C-shaped arm device for the X-ray device according to the embodiments of the present disclosure may include but be not limited to: (1) a lift assembly capable of adjusting the distance between the detector and the radiation source may be provided; (2) the lift assembly includes two or more arm sections, and the moving path length of the target arm section may be twice that of the previous arm section (for example, the intermediate arm section) through the linkage assembly between the two adjacent arm sections, so that the shell supporting the intermediate arm section may have a relatively small size, thereby realizing a relatively large moving path length of the target arm section; (3) the C-shaped arm device using the aforementioned lift assembly may achieve a compact structure, and may release a part of an operation space of the C-shaped arm device, so as to satisfy the needs of a large opening and a large operation space for the C-shaped arm in the clinical operation.

In some embodiments, the scanning apparatus (or the C-shaped arm device) may effectively change the FOV (e.g., the first reconstruction FOV, the second reconstruction FOV) of the scanning apparatus by adjusting the distance between the detector and the radiation source through the lift assembly. For example, an increase of the distance between the detector and the radiation source may increase the FOV, and a decrease of the distance between the detector and the radiation source may reduce the FOV. In some embodiments, the scanning apparatus may not only adjust the distance between the detector and the radiation source through the lift assembly, but also scan the target object in the deflected state, so that the scanning apparatus may obtain a suitable view and the imaging quality may be improved. In addition, the structure of the scanning apparatus may be compact, which is more convenient for the clinical operation. In some embodiments, the scanning apparatus may not only adjust the distance between the detector and the radiation source through the lift assembly, but also enable the radiation source to move in the first direction while performing a circular scanning motion, so that the scanning apparatus may use a suitable SID for the scanning and collect more complete information during the scanning process, thereby effectively improving the image reconstruction effect. In some embodiments, the scanning apparatus may not only adjust the distance between the detector and the radiation source through the lift assembly, but also may scan the target object in the deflected state, and may also make the radiation source to move in the first direction while performing a circular scanning motion, so that the scanning apparatus may be adaptable to more application scenarios and requirements, and effectively improve the scanning quality in each scenario.

The above descriptions are only preferred embodiments of the present disclosure and are not intended to limit the scope of the present disclosure. Any modifications, equivalent replacements, and improvements made within the spirit and principles of the present disclosure shall be included in the protection scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A scanning apparatus, including a gantry, a controller, a C-shaped arm, a radiation source, and a detector, wherein
the radiation source and the detector are arranged at both ends of the C-shaped arm,
the C-shaped arm is connected to the gantry, and
the controller is configured to control a motion of the gantry to drive the C-shaped arm to move so as to scan a target object,
wherein under the control of the controller, the radiation source at one end of the C-shaped arm is configured to move in a first direction while performing a circular scanning motion, the first direction forms a first included angle with a perpendicular line of a circumferential plane formed when the radiation source has a circular motion, and the first included angle is smaller than a preset threshold.

2. The scanning apparatus of claim 1, wherein the scanning apparatus is a cone-beam computed tomography scanning apparatus, and the gantry has a deflection mode and a rotation mode, wherein
in the deflection mode, the gantry drives the radiation source and the detector to deflect around a center point of the detector, or
in the rotation mode, the gantry drives the radiation source and the detector to rotate around a center of interest of the target object to scan the target object and obtain scanning data of the target object,
wherein the radiation source and the detector have a first reconstruction field of view (FOV) before the deflection, the radiation source and the detector have a second reconstruction FOV after the deflection, and the second reconstruction FOV is larger than the first reconstruction FOV.

3. The scanning apparatus of claim 2, wherein a scanning view of a single frame after the deflection of the radiation source and the detector covers at least half of the second reconstruction FOV.

4. The scanning apparatus of claim 1, wherein under the control of the controller, the radiation source is configured to scan along a spiral trajectory.

5. The scanning apparatus of claim 1, wherein under the control of the controller, the radiation source alternately performs a circular motion in a clockwise direction and a counterclockwise direction while moving in the first direction, so that the radiation source scans along a reciprocating spiral trajectory.

6. The scanning apparatus of claim 1, wherein the first direction is an extension direction of a scanning bed.

7. The scanning apparatus of claim 1, wherein the controller is configured to control the radiation source to move in the first direction while performing the circular scanning motion within a scanning range, and the scanning range covers a target scanning range.

8. The scanning apparatus of claim 1, wherein at least one of the detector or the radiation source is connected to the C-shaped arm through a lift assembly, the lift assembly comprising:
a shell;
a driving assembly accommodated in the shell; and
an arm adjustment assembly, the arm adjustment assembly moving under a driving of the driving assembly, wherein
the arm adjustment assembly includes an intermediate arm section, a target arm section, and a linkage assembly disposed between the intermediate arm section and the target arm section,
the intermediate arm section moves in a first direction under the driving of the driving assembly,
when the intermediate arm section moves in the first direction, the target arm section is driven to move in the first direction by the linkage assembly,
projections of the intermediate arm section and the target arm section respectively in the first direction at least partially overlap, and
the target arm section is connected to the detector or the radiation source.

9. The scanning apparatus of claim 8, wherein,
the linkage assembly includes a first support component and a second support component arranged on the intermediate arm section, a first flexible traction component connected to the first support component, and a second flexible traction component connected to the second support component;

one end of the first flexible traction component is connected to the shell, the other end of the first flexible traction component is connected to the target arm section; one end of the second flexible traction component is connected to the shell, and the other end of the second flexible traction component is connected to the target arm section.

10. The scanning apparatus of claim 8, wherein the linkage assembly further includes:
a first sliding block, and
a first guiding rail matched with the first sliding block, wherein the first sliding block is arranged on one of the intermediate arm section and the target arm section, and the first guiding rail is arranged on the other one of the intermediate arm section and the target arm section.

11. The scanning apparatus of claim 8, wherein the lift assembly further includes:
a transmission assembly disposed between the driving assembly and the intermediate arm section configured for a transmission between the driving assembly and the intermediate arm section.

12. The scanning apparatus of claim 11, wherein the transmission assembly includes a screw nut structure.

13. The scanning apparatus of claim 12, wherein the screw nut structure includes:
a nut rotatable relative to the shell, and
a screw located at a fixed location relative to the intermediate arm section, wherein the nut is threadedly connected to the screw, and the nut is driven by the driving assembly.

14. The scanning apparatus of claim 8, wherein the lift assembly further includes: a second sliding block disposed between the shell and the intermediate arm section, and a second guiding rail matched with the second sliding block, wherein the second sliding block is arranged on one of the shell and the intermediate arm section, and the second guiding rail is arranged on the other one of the shell and the intermediate arm section.

15. A method for obtaining a medical image, wherein the method is implemented by a cone-beam computed tomography scanning apparatus, the cone-beam computed tomography scanning apparatus includes a radiation source and a detector; the method comprising:
deflecting the radiation source and the detector around a center point of the detector; and
rotating the deflected radiation source and the deflected detector around a center of interest of a target object to scan the target object and obtain scanning data of the target object,
wherein the radiation source and the detector have a first reconstruction FOV before the deflection, the radiation source and the detector have a second reconstruction FOV after the deflection, and the second reconstruction FOV is larger than the first reconstruction FOV.

16. The method of claim 15, wherein the second reconstruction FOV includes a repeatedly scanned area, and the method further comprises:
reconstructing the scanning data of the target object to obtain a reconstruction image of the target object, wherein the reconstruction image includes an image region corresponding to the repeatedly scanned area, and the image region is reconstructed by weighting the scanning data of the repeatedly scanned area based on a preset weight curve.

17. The method of claim 16, wherein the preset weight curve relates to positions at the detector corresponding to the repeatedly scanned area, and the preset weight curve is determined by:
determining, starting from the radiation source, two tangent lines tangent to the repeatedly scanned area, the two tangent lines passing through a first point and a second point of the detector, respectively;
determining, starting from the radiation source, a straight line passing through the center of interest and a third point of the detector, wherein the first point is located at an edge of the detector, the second point is located in a non-edge area of the detector, and the third point is located between the first point and the second point;
setting a weight of the scanning data corresponding to the first point as a;
setting a weight of the scanning data corresponding to the second point as b;
setting a weight of the scanning data corresponding to the third point as c, wherein, $0 \leq a < c < b \leq 1$, and
determining a weight curve from the first point to the second point of the detector as the preset weight curve according to the set weights.

18. The scanning apparatus of claim 2, wherein the cone-beam computed tomography scanning apparatus is a digital subtraction angiography scanner or a mobile C-shaped arm machine.

19. The scanning apparatus of claim 2, wherein a deflection angle of the deflection is adjustable.

20. The scanning apparatus of claim 1, wherein the gantry comprises a base and a robotic arm assembly, the C-shaped arm is rotatably arranged at one end of the robotic arm assembly away from the base.

* * * * *